United States Patent
Yu et al.

(10) Patent No.: US 9,815,870 B2
(45) Date of Patent: Nov. 14, 2017

(54) MONOMERIC AND BRIGHT INFRARED FLUORESCENT PROTEINS

(71) Applicant: THE REGENTS OF THE UNIVERSITY OF CALIFORNIA, Oakland, CA (US)

(72) Inventors: Dan Yu, San Francisco, CA (US); Xiaokun Shu, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/764,727

(22) PCT Filed: Jan. 30, 2014

(86) PCT No.: PCT/US2014/013912
§ 371 (c)(1),
(2) Date: Jul. 30, 2015

(87) PCT Pub. No.: WO2014/120959
PCT Pub. Date: Aug. 7, 2014

(65) Prior Publication Data
US 2015/0353609 A1   Dec. 10, 2015

Related U.S. Application Data

(60) Provisional application No. 61/758,368, filed on Jan. 30, 2013.

(51) Int. Cl.
| | |
|---|---|
| C07K 1/00 | (2006.01) |
| C07K 14/195 | (2006.01) |
| G01N 33/52 | (2006.01) |
| A61K 49/00 | (2006.01) |

(52) U.S. Cl.
CPC ........ *C07K 14/195* (2013.01); *A61K 49/0045* (2013.01); *G01N 33/52* (2013.01); *C07K 2319/00* (2013.01)

(58) Field of Classification Search
CPC .................................................. C07K 14/195
See application file for complete search history.

(56) References Cited

U.S. PATENT DOCUMENTS

| | | | |
|---|---|---|---|
| 4,673,641 A | 6/1987 | George et al. | |
| 5,776,689 A | 7/1998 | Karin et al. | |
| 8,735,555 B2* | 5/2014 | Lagarias | C07K 14/415 530/370 |
| 2009/0300793 A1* | 12/2009 | Lagarias | C07K 14/415 800/278 |
| 2011/0003974 A1 | 1/2011 | Lukyanov et al. | |

FOREIGN PATENT DOCUMENTS

WO   WO 2014/120959   8/2014

OTHER PUBLICATIONS

Altschul, S. et al., "Basic Local Alignment Search Tool", *J. Mol. Biol.*, vol. 215, pp. 403-410 (1990).
Altschul, S. et al., "Gapped BLAST and PSI-BLAST: a new generation of protein database search programs", *Nucleic Acids Research*, vol. 25, No. 17, pp. 3389-3402 (1997).
Batzer, M. et al., "Enhanced evolutionary PCR using oligonucleotides with inosine at the 3'-terminus", *Nucleic Acids Research*, vol. 19, No. 18, p. 5081 (1991).
Bellini and Papiz, "Dimerization properties of the RpBphP2 chromophore-binding domain crystallized by homologue-directed mutagenesis." Research Papers, Acta Cryst, D68, 1058-1066 (2012).
Berkelman and Lagarias, "Visualization of bilin-linked peptides and proteins in polyacrylamide gels." Analytical Biochemistry 156, 194-201 (1986).
Buss et al., "The six amino-terminal amino acids of p60src are sufficient to cause myristylation of p21v-ras." Mol. Cell. Biol. 8:3960-3963 (1988).
Chalfie, M., et al., "Green fluorescent protein as a marker for gene expression." Science 263:802-805 (1994).
Cody et al., "Chemical structure of the hexapeptide chromophore of the Aequorea green-fluorescent protein." Biochemistry 32:1212-1218 (1993).
Cui, L. et al. "Relevant expression of *Drosophila* heme oxygenase is necessary for the normal development of insect tissues." Biochemical and Biophysical Research Communications. Biochem Biophys Res Commun 377, 1156-1161 (2008).
Day and Davidson, "The fluorescent protein palette: tools for cellular imaging." Chem Soc Rev 38, 2887-2921 (2009).
Fischer and Lagarias, Proc. Natl. Acad. Sci. U.S.A., "Harnessing phytochrome's glowing potential." 101, 17334 (2004).
Filonov, G. S. et al. "Bright and stable near-infrared fluorescent protein for in vivo imaging." Nat Biotechnol 29, 757-761 (2011).
Giraud et al., "Bacteriophytochrome controls photosystem synthesis in anoxygenic bacteria." Nature 417:202-205 (2002).
Giraud and Verméglio, "Bacteriophytochromes in anoxygenic photosynthetic bacteria." Photosyn Res 97, 141-153 (2008).
Gossen and Bujard, " Tight control of gene expression in mammalian cells by tetracycline-responsive promoters." PNAS 89:5547 (1992).
Hancock et al., "A CAAX or a CAAL motif and a second signal are sufficient for plasma membrane targeting of ras proteins." EMBO J. 10:4033-4039 (1991).
Heim et al., "Wavelength mutations and posttranslational autoxidation of green fluorescent protein." PNAS USA, 91(26):12501-4 (1994).

(Continued)

*Primary Examiner* — Albert Navarro
(74) *Attorney, Agent, or Firm* — Morgan, Lewis & Bockius LLP; Jeffry S. Mann

(57) ABSTRACT

The invention described herein features variants related to infrared fluorescent proteins, in particular to mutants of a phytochrome from the bacterium *Bradyrhizobium* sp. ORS278. The variants show approximately a ten-fold increase in brightness compared to other known infrared fluorescent proteins. The variants are monomeric, allowing them to be used as a protein tag without disrupting the function of the tagged protein of interest.

7 Claims, 15 Drawing Sheets

(56) References Cited

OTHER PUBLICATIONS

Heim and Tsien, "Engineering green fluorescent protein for improved brightness, longer wavelengths and fluorescence resonance energy transfer." Curr. Biol. 6:178-182 (1996).
Henikoff, S. and Henikoff, J., "Amino acid substitution matrices from protein blocks", Proc. Natl., Acad. Sci. USA, vol. 89, pp. 10915-10919 (1992).
Jacak et al., "Computational protein design with explicit consideration of surface hydrophobic patches." Proteins 80, 825-838 (2011).
Jöbsis, F.F., "Noninvasive, infrared monitoring of cerebral and myocardial oxygen sufficiency and circulatory parameters." Science, 198, 1264 (1977).
Kakitani, T. and Kakitani, H. "Theoretical Study of Optical Spectra and Conformation of the Chromophore of Hypsorhodopsin." Photochem Photobiol 32, 707-709 (1980).
Karniol et al., "Phylogenetic analysis of the phytochrome superfamily reveals distinct microbial subfamilies of photoreceptors." Biochem J 392, 103 (2005).
Kremers et al., "Fluorescent proteins at a glance." Journal of Cell Science 124, 2676-2676 (2011).
Lee and Richards, "The interpretation of protein structures: estimation of static accessibility." J Mol Biol 55, 379-400 (1971).
Livet, J. et al. "Transgenic strategies for combinatorial expression of fluorescent proteins in the nervous system." Nature 450, 56-62 (2007).
McCafferty, J. et al., "Phage antibodies: filamentous phage displaying antibody variable domains", Nature, vol. 348, pp. 552-554 (1990).
Miyawaki, A. et al., "Fluorescent indicators for Ca2+ based on green fluorescent proteins and calmodulin." Nature 388, 882-887 (1997).
Morise, H., et al., "Intermolecular energy transfer in the bioluminescent system of Aequorea" Biochemistry 13:2656-2662 (1974).
Moelbert, S. et al., "Correlation between sequence hydrophobicity and surface-exposure pattern of database proteins." Protein Science 13, 752-762 (2004).
Needleman, S. et al., "A General Method Applicable to the Search for Similarities in the Amino Acid Sequence of Two Proteins", J. Mol. Biol., vol. 48, pp. 443-453 (1970).
Neering et al., "Transduction of primitive human hematopoietic cells with recombinant adenovirus vectors." Blood 88:1147-1155 (1996).
Ohtsuka, E. et al., "An Alternative Approach to Deoxyoligonucleotides as Hybridization Probes by Insertion of Deoxyinosine at Ambiguous Codon Positions", The Journal of Biological Chemistry, vol. 260, No. 5, pp. 2605-2608 (1985).
Olingo et al.,"Drug inducible transgene expression in brain using a herpes simplex virus vector." Gene Ther. 5:491-496 (1998).
Ormö, M., et al., "Crystal structure of the Aequorea victoria green fluorescent protein." Science 273:1392-1395 (1996).
Pearson and Lipman, "Improved tools for biological sequence comparison", Proc. Natl. Acad. Sci. USA, vol. 85, pp. 2444-2448 (1988).
Poss and Tonegawa, "Heme oxygenase 1 is required for mammalian iron reutilization." Proc Natl Acad Sci USA 94, 10919-10924 (1997).
Prasher et al., "Primary structure of the Aequorea victoria green-fluorescent protein." Gene 111:229-233 (1992).
Prendergrast and Mann, "Chemical and physical properties of aequorin and the green fluorescent protein isolated from Aequorea forskålea." Biochemistry 17:3448-3453 (1978).
Rendahl et al., "Regulation of gene expression in vivo following transduction by two separate rAAV vectors." Nat. Biotechnol. 16:757-761 (1998).
Rockwell, N. C. "The Structure of Phytochrome: A Picture Is Worth a Thousand Spectra." The Plant Cell Online 18, 4-14 (2006).
Rossolini et al., "Use of deoxyinosine-containing primers vs degenerate primers for polymerase chain reaction based on ambiguous sequence information." Mol. Cell. Probes 8:91-98 (1994).
Sakaue-Sawano et al. "Visualizing Spatiotemporal Dynamics of Multicellular Cell-Cycle Progression." Cell 132, 487-498 (2008).
Schwede, T. et al, "Swiss-Model: an automated protein homology-modeling server." Nucleic Acids Res 31, 3381-3385 (2003).
Shcherbo et al., "Bright far-red fluorescent protein for whole-body imaging." Nat. Methods, 4(9):741 (2007).
Shu, X. et al. "Mammalian expression of infrared fluorescent proteins engineered from a bacterial phytochrome." Science 324, 804-807 (2009).
Shkrob et al., "Far-red fluorescent proteins evolved from a blue chromoprotein from Actinia equina." Biochem. J. 392, 649 (2005).
Smith and Waterman, "Comparison of Biosequences", Advances in Applied Mathematics, vol. 2, pp. 482-489 (1981).
Tsien, R. Y. "Constructing and exploiting the fluorescent protein paintbox." (Nobel Lecture). Angew Chem Int Ed Engl 48, 5612-5626 (2009).
Ulijasz and Vierstra, "Phytochrome structure and photochemistry: recent advances toward a complete molecular picture." Curr Opin Plant Biol 14, 498-506 (2011).
Wagner et al., "A light-sensing knot revealed by the structure of the chromophore-binding domain of phytochrome." Nature 438, 325-331 (2005).
Wagner et al., "High Resolution Structure of Deinococcus Bacteriophytochrome Yields New Insights into Phytochrome Architecture and Evolution." J Biol Chem 282, 12298-12309 (2007).
Wang and Hazelrigg, "Implications for bcd mRNA localization from spatial distribution of exu protein in Drosophila oogenesis." Nature, 369:400-403 (1994).
Wang et al., "Positive and negative regulation of gene expression in eukaryotic cells with an inducible transcriptional regulator." Gene Ther. 4:432-441 (1997).
Wang et al., "Evolution of new nonantibody proteins via iterative somatic hypermutation." PNAS USA, 101, 16745 (2004).
Wang, Y. et al. Visualizing the mechanical activation of Src. Nature 434, 1040-1045 (2005).
Ward and Cormier, "Energy transfer via protein-protein interaction in Renilla bioluminescence." Photochem. Photobiol. 27:389-396 (1978).
Ward, W., "Spectral Perturbations of the Aequorea Green-Fluorescent Protein", Photochem. Photobiol. Rev. 4:1-57 (1982).
Ward, W. et al., "Spectrophotometric identity of the energy transfer chromophores in Renilla and Aequorea green fluorescent proteins." Photochem. Photobiol. Rev. 31:611-615 (1980).
Weissleder and Ntziachristos, "Shedding light onto live molecular targets." Nat. Med. 9, 123 (2003).
Yang, F. et al., "The molecular structure of green fluorescent protein." Nature Biotech. 14:1246-1251 (1996).
Yang, X. et al., "Temperature-scan cryocrystallography reveals reaction intermediates in bacteriophytochrome." Nature 479, 428-432 (2011).
Yang, X. et al.,"Crystal structure of the chromophore binding domain of an unusual bacteriophytochrome, RpBphP3, reveals residues that modulate photoconversion." Proc Natl Acad Sci USA 104, 12571-12576 (2007).
Yokoe and Meyer, "Spatial dynamics of GFP-tagged proteins investigated by local fluorescence enhancement." Nature Biotech. 14:1252-1256 (1996).
Zaccolo, M., "Discrete Microdomains with High Concentration of cAMP in Stimulated Rat Neonatal Cardiac Myocytes." Science 295, 1711-1715 (2002).
Zhang, J. et al., "Insulin disrupts beta-adrenergic signaling to protein kinase A in adipocytes." Nature 437, 569-573 (2005).
GenBank accession No. AAL68700.1 (2004).
GenBank accession No. CAL75507.1 (2010).
GenBank accession No. CCD96378.1 (2013).
GenBank accession No. YP_001203744.1 (2013).
GenBank accession No. WP_011924736.1 (2013).

* cited by examiner

DNA sequence of mIFP

SEQ ID NO:1
ATGTCGGTACCGCTGACTACCTCAGCATTCGGCCACGCGTTTCTGGCTAACTGTGAACGCGAGCA
GATCCACCTGGCGGGCTCCATTCAGCCGCACGGTATCCTGCTGGCTGTGAAAGAGCCGGACAACG
TGGTGATCCAGGCTTCTATTAACGCTGCGGAGTTCCTGAACACCAACTCTGTTGTTGGCCGTCCG
CTGCGTGACCTGGGCGGCGATCTGCCTTTGCAGATCCTGCCGCACCTGAACGGCCCGCTGCACCT
GGCTCCGATGACCCTGCGTTGTACCGTGGGTTCTCCGCCGCGTCGTGTGGACTGTACCATTCATC
GTCCGTCTAACGGCGGCCTGATCGTAGAACTGGAACCAGCAACCAAGACCACTAACATTGCGCCG
GCTCTGGACGGTGCGTTTCATCGTATCACTTCTTCATCCTCCCTGATGGGCCTGTGTGACGAAAC
CGCGACTATTATCCGTGAGATTACTGGCTACGACCGTGTGATGGTAGTACGTTTCGATGAAGAGG
GTAATGGCGAAATTCTGTCCGAACGTCGTCGTGCGGACCTGGAAGCGTTCCTGGGTAACCGCTAC
CCGGCGTCTACTATTCCGCAGATCGCTCGTCGCCTGTACGAACATAACCGTGTTCGCCTGCTGGT
AGATGTGAACTATACTCCGGTTCCGCTACAGCCGCGCATCAGCCCGCTGAACGGTCGTGATCTGG
ATATGTCCCTGTCTTGCCTGCGCTCTATGTCCCCGATCCACCAGAAATACATGCAGGACATGGGC
GTTGGCGCGACCCTGGTTTGCTCTCTGATGGTGTCTGGTCGTCTGTGGGGTCTGATCGCTTGCCA
CCACTACGAACCGCGCTTCGTTCCGTTCCACATTCGCGCTGCTGGCGAAGCGCTGGCGGAAACTT
GTGCGATCCGCATCGCGACGCTGGAGAGCTTTGCACAGTCTCAGTCCAAA

Protein sequence of mIFP

SEQ ID NO:2
MSVPLTTSAFGHAFLANCEREQIHLAGSIQPHGILLAVKEPDNVVIQASINAAEFLNTNSVVGRP
LRDLGGDLPLQILPHLNGPLHLAPMTLRCTVGSPPRRVDCTIHRPSNGGLIVELEPATKTTNIAP
ALDGAFHRITSSSSLMGLCDETATIIREITGYDRVMVVRFDEEGNGEILSERRRADLEAFLGNRY
PASTIPQIARRLYEHNRVRLLVDVNYTPVPLQPRISPLNGRDLDMSLSCLRSMSPIHQKYMQDMG
VGATLVCSLMVSGRLWGLIACHHYEPRFVPFHIRAAGEALAETCAIRIATLESFAQSQSK

BrCDB to mIFP amino acid substitutions

```
BrCBD   MPVPLTTPAFGHATLANCEREQIHLAGSIQPHGILLAVKEPDNVVIQASI
mIFP    MSVPLTTSAFGHAFLANCEREQIHLAGSIQPHGILLAVKEPDNVVIQASI

BrCBD   NAAEFLNTNSVVGRPLRDLGGDLALQILPHLNGPLHLAPMTLRCTVGSPP
mIFP    NAAEFLNTNSVVGRPLRDLGGDLPLQILPHLNGPLHLAPMTLRCTVGSPP

BrCBD   RRVDCTVHRPSNGGLIVELEPATKTTNVAPALDGAFHRITSSSSLIGLCD
mIFP    RRVDCTIHRPSNGGLIVELEPATKTTNIAPALDGAFHRITSSSSLMGLCD

BrCBD   ETATIFREITGYDRVMVYRFDEEGHGEVLSERRRPDLEAFLGNRYPASDI
mIFP    ETATIIREITGYDRVMVVRFDEEGNGEILSERRRADLEAFLGNRYPASTI

BrCBD   PQIARRLYERNRVRLLVDVNYTPVPLQPRISPLNGRDLDMSLSCLRSMSP
mIFP    PQIARRLYEHNRVRLLVDVNYTPVPLQPRISPLNGRDLDMSLSCLRSMSP

BrCBD   IHQKYLQNMGVGATLVCSLMVSGRLWGLIACHHYEPRFVPFDIRAAGEAL
mIFP    IHQKYMQDMGVGATLVCSLMVSGRLWGLIACHHYEPRFVPFHIRAAGEAL

BrCBD   AETCAIRIAALESFAQSQSE
mIFP    AETCAIRIATLESFAQSQSK
```

FIGURE 2

SEQUENCE LISTING

<160> NUMBER OF SEQ ID NOS: 26

<210> SEQ ID NO 1
<211> LENGTH: 960
<212> TYPE: DNA
<213> ORGANISM: Artificial Sequence
<220> FEATURE:
<223> OTHER INFORMATION: nucleic acid sequence of mIFP

<400> SEQUENCE: 1

```
atgtcggtac cgctgactac ctcagcattc ggccacgcgt ttctggctaa ctgtgaacgc    60
gagcagatcc acctggcggg ctccattcag ccgcacggta tcctgctggc tgtgaaagag   120
ccggacaacg tggtgatcca ggcttctatt aacgctgcgg agttcctgaa caccaactct   180
gttgttggcc gtccgctgcg tgacctgggc ggcgatctgc ctttgcagat cctgccgcac   240
ctgaacggcc cgctgcacct ggctccgatg accctgcgtt gtaccgtggg ttctccgccg   300
cgtcgtgtgg actgtaccat tcatcgtccg tctaacggcg gcctgatcgt agaactggaa   360
ccagcaacca agaccactaa cattgcgccg gctctggacg gtgcgtttca tcgtatcact   420
tcttcatcct ccctgatggg cctgtgtgac gaaaccgcga ctattatccg tgagattact   480
ggctacgacc gtgtgatggt agtacgtttc gatgaagagg gtaatggcga aattctgtcc   540
gaacgtcgtc gtgcggacct ggaagcgttc ctgggtaacc gctacccggc gtctactatt   600
ccgcagatcg ctcgtcgcct gtacgaacat aaccgtgttc gcctgctggt agatgtgaac   660
tatactccgg ttccgctaca gccgcgcatc agcccgctga acggtcgtga tctggatatg   720
tccctgtctt gcctgcgctc tatgtccccg atccaccaga aatacatgca ggacatgggc   780
gttggcgcga ccctggtttg ctctctgatg gtgtctggtc gtctgtgggg tctgatcgct   840
tgccaccact acgaaccgcg cttcgttccg ttccacattc gcgctgctgg cgaagcgctg   900
gcggaaactt gtgcgatccg catcgcgacg ctggagagct ttgcacagtc tcagtccaaa   960
```

<210> SEQ ID NO 2
<211> LENGTH: 320
<212> TYPE: PRT
<213> ORGANISM: Artificial Sequence
<220> FEATURE:
<223> OTHER INFORMATION: amino acid sequence of mIFP

<400> SEQUENCE: 2

```
Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
```

```
                130                 135                 140
Leu Met Gly Leu Cys Asp Glu Thr Ala Thr Ile Ile Arg Glu Ile Thr
145                 150                 155                 160
Gly Tyr Asp Arg Val Met Val Val Arg Phe Asp Glu Glu Gly Asn Gly
                165                 170                 175
Glu Ile Leu Ser Glu Arg Arg Ala Asp Leu Glu Ala Phe Leu Gly
            180                 185                 190
Asn Arg Tyr Pro Ala Ser Thr Ile Pro Gln Ile Ala Arg Arg Leu Tyr
                195                 200                 205
Glu His Asn Arg Val Arg Leu Leu Val Asp Val Asn Tyr Thr Pro Val
            210                 215                 220
Pro Leu Gln Pro Arg Ile Ser Pro Leu Asn Gly Arg Asp Leu Asp Met
225                 230                 235                 240
Ser Leu Ser Cys Leu Arg Ser Met Ser Pro Ile His Gln Lys Tyr Met
                245                 250                 255
Gln Asp Met Gly Val Gly Ala Thr Leu Val Cys Ser Leu Met Val Ser
            260                 265                 270
Gly Arg Leu Trp Gly Leu Ile Ala Cys His His Tyr Glu Pro Arg Phe
        275                 280                 285
Val Pro Phe His Ile Arg Ala Ala Gly Glu Ala Leu Ala Glu Thr Cys
            290                 295                 300
Ala Ile Arg Ile Ala Thr Leu Glu Ser Phe Ala Gln Ser Gln Ser Lys
305                 310                 315                 320

<210> SEQ ID NO 3
<211> LENGTH: 320
<212> TYPE: PRT
<213> ORGANISM: Artificial Sequence
<220> FEATURE:
<223> OTHER INFORMATION: BrIFPv1, amino acid sequence

<400> SEQUENCE: 3

Met Pro Val Pro Leu Thr Thr Pro Ala Phe Gly His Ala Thr Leu Ala
1               5                   10                  15
Asn Cys Glu Arg Glu Gln Ile His Leu Ala Gly Ser Ile Gln Pro His
            20                  25                  30
Gly Ile Leu Leu Ala Val Lys Glu Pro Asp Asn Val Val Ile Gln Ala
        35                  40                  45
Ser Ile Asn Ala Ala Glu Phe Leu Asn Thr Asn Ser Val Val Gly Arg
    50                  55                  60
Pro Leu Arg Asp Leu Gly Gly Asp Leu Ala Leu Gln Ile Leu Pro His
65                  70                  75                  80
Leu Asn Gly Pro Leu His Leu Ala Pro Met Thr Leu Arg Cys Thr Val
                85                  90                  95
Gly Ser Pro Pro Arg Arg Val Asp Cys Thr Val His Arg Pro Ser Asn
            100                 105                 110
Gly Gly Leu Ile Val Glu Leu Glu Pro Ala Thr Lys Thr Thr Asn Val
        115                 120                 125
Ala Pro Ala Leu Asp Gly Ala Phe His Arg Ile Thr Ser Ser Ser Ser
    130                 135                 140
Leu Ile Gly Leu Cys Asp Glu Thr Ala Thr Ile Phe Arg Glu Ile Thr
145                 150                 155                 160
Gly Tyr Asp Arg Val Met Val Tyr Arg Phe Asp Glu Glu Gly His Gly
                165                 170                 175
Glu Val Leu Ser Glu Arg Arg Arg Pro Asp Leu Glu Ala Phe Leu Gly
```

```
            180                 185                 190
Asn Arg Tyr Pro Ala Ser Met Ile Pro Gln Ile Ala Arg Arg Leu Tyr
            195                 200                 205

Glu Arg Asn Arg Val Arg Leu Leu Val Asp Val Asn Tyr Thr Pro Val
            210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Ile His Gln Lys Tyr Leu
            245                 250                 255

Gln Asn Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
            275                 280                 285

Val Pro Phe Asp Ile Arg Ala Ala Gly Glu Ala Leu Ala Glu Thr Cys
            290                 295                 300

Ala Ile Arg Ile Ala Ala Leu Glu Ser Phe Ala Gln Ser Gln Ser Glu
305                 310                 315                 320

<210> SEQ ID NO 4
<211> LENGTH: 960
<212> TYPE: PRT
<213> ORGANISM: Artificial Sequence
<220> FEATURE:
<223> OTHER INFORMATION: BrIFPv1, nucleic acid sequence

<400> SEQUENCE: 4

Ala Thr Gly Cys Cys Gly Gly Thr Ala Cys Cys Gly Cys Thr Gly Ala
1               5                   10                  15

Cys Thr Ala Cys Cys Cys Cys Gly Gly Cys Ala Thr Thr Cys Gly Gly
            20                  25                  30

Cys Cys Ala Cys Gly Cys Gly Ala Cys Thr Cys Thr Gly Gly Cys Thr
        35                  40                  45

Ala Ala Cys Thr Gly Thr Gly Ala Ala Cys Gly Cys Gly Ala Gly Cys
    50                  55                  60

Ala Gly Ala Thr Cys Cys Ala Cys Cys Thr Gly Gly Cys Gly Gly Gly
65                  70                  75                  80

Cys Thr Cys Cys Ala Thr Thr Cys Ala Gly Cys Cys Gly Cys Ala Cys
            85                  90                  95

Gly Gly Thr Ala Thr Cys Cys Thr Gly Cys Thr Gly Cys Thr Gly Gly
            100                 105                 110

Thr Gly Ala Ala Ala Gly Ala Gly Cys Cys Gly Gly Ala Cys Ala Ala
        115                 120                 125

Cys Gly Thr Gly Gly Thr Gly Ala Thr Cys Cys Ala Gly Gly Cys Thr
    130                 135                 140

Thr Cys Thr Ala Thr Thr Ala Ala Cys Gly Cys Thr Gly Cys Gly Gly
145                 150                 155                 160

Ala Gly Thr Thr Cys Cys Thr Gly Ala Ala Cys Ala Cys Cys Ala Ala
            165                 170                 175

Cys Thr Cys Thr Gly Thr Thr Gly Thr Thr Gly Gly Cys Cys Gly Thr
            180                 185                 190

Cys Cys Gly Cys Thr Gly Cys Gly Thr Gly Ala Cys Cys Thr Gly Gly
        195                 200                 205

Gly Cys Gly Gly Cys Gly Ala Thr Cys Thr Gly Gly Cys Thr Cys Thr
    210                 215                 220

Gly Cys Ala Gly Ala Thr Cys Cys Thr Gly Cys Cys Gly Cys Ala Cys
```

-continued

```
225                 230                 235                 240

Cys Thr Gly Ala Ala Cys Gly Gly Cys Cys Cys Gly Cys Thr Gly Cys
                245                 250                 255

Ala Cys Cys Thr Gly Gly Cys Thr Cys Cys Gly Ala Thr Gly Ala Cys
            260                 265                 270

Cys Cys Thr Gly Cys Gly Thr Thr Gly Thr Ala Cys Cys Gly Thr Gly
        275                 280                 285

Gly Gly Thr Thr Cys Thr Cys Cys Gly Cys Cys Gly Cys Gly Thr Cys
    290                 295                 300

Gly Thr Gly Thr Gly Gly Ala Cys Thr Gly Thr Ala Cys Cys Gly Thr
305                 310                 315                 320
Thr Cys Ala Thr Cys Gly Thr Cys Cys Gly Thr Cys Thr Ala Ala Cys
                325                 330                 335
Gly Gly Cys Gly Gly Cys Cys Thr Gly Ala Thr Cys Gly Thr Ala Gly
            340                 345                 350
Ala Ala Cys Thr Gly Gly Ala Ala Cys Cys Gly Gly Cys Ala Ala Cys
        355                 360                 365

Cys Ala Ala Gly Ala Cys Cys Ala Cys Thr Ala Ala Cys Gly Thr Thr
    370                 375                 380

Gly Cys Gly Cys Cys Gly Gly Cys Thr Cys Thr Gly Gly Ala Cys Gly
385                 390                 395                 400

Gly Thr Gly Cys Gly Thr Thr Thr Cys Ala Thr Cys Gly Thr Ala Thr
                405                 410                 415

Cys Ala Cys Thr Thr Cys Thr Thr Cys Cys Thr Cys Cys Thr Cys Cys
            420                 425                 430

Cys Thr Gly Ala Thr Cys Gly Gly Cys Cys Thr Gly Thr Gly Thr Gly
        435                 440                 445

Ala Cys Gly Ala Ala Ala Cys Cys Gly Cys Gly Ala Cys Thr Ala Thr
    450                 455                 460

Thr Thr Thr Cys Cys Gly Thr Gly Ala Gly Ala Thr Thr Ala Cys Thr
465                 470                 475                 480

Gly Gly Cys Thr Ala Cys Gly Ala Cys Cys Gly Thr Gly Thr Gly Ala
                485                 490                 495

Thr Gly Gly Thr Ala Thr Ala Cys Cys Gly Thr Thr Thr Cys Gly Ala
            500                 505                 510

Thr Gly Ala Ala Gly Ala Gly Gly Gly Thr Cys Ala Thr Gly Gly Cys
        515                 520                 525

Gly Ala Ala Gly Thr Gly Cys Thr Gly Thr Cys Cys Gly Ala Ala Cys
    530                 535                 540

Gly Thr Cys Gly Thr Cys Gly Thr Cys Cys Gly Gly Ala Cys Cys Thr
545                 550                 555                 560

Gly Gly Ala Ala Gly Cys Gly Thr Thr Cys Cys Thr Gly Gly Gly Thr
                565                 570                 575

Ala Ala Cys Cys Gly Cys Thr Ala Cys Cys Cys Gly Gly Cys Gly Thr
            580                 585                 590

Cys Thr Ala Thr Gly Ala Thr Thr Cys Cys Gly Cys Ala Gly Ala Thr
        595                 600                 605

Cys Gly Cys Thr Cys Gly Thr Cys Gly Cys Cys Thr Gly Thr Ala Cys
    610                 615                 620

Gly Ala Ala Cys Gly Thr Ala Ala Cys Cys Gly Thr Gly Thr Thr Cys
625                 630                 635                 640

Gly Cys Cys Thr Gly Cys Thr Gly Gly Thr Ala Gly Ala Thr Gly Thr
                645                 650                 655
```

-continued

Gly Ala Ala Cys Thr Ala Thr Ala Cys Thr Cys Cys Gly Thr Thr
              660                 665                 670

Cys Cys Gly Cys Thr Gly Cys Ala Gly Cys Cys Gly Cys Gly Ala
              675                 680                 685

Thr Cys Ala Gly Cys Cys Gly Cys Thr Gly Ala Ala Cys Gly Gly
              690                 695                 700

Thr Cys Gly Thr Gly Ala Cys Cys Thr Gly Ala Thr Ala Thr Gly
705                 710                 715                 720

Thr Cys Cys Cys Thr Gly Thr Cys Thr Thr G

```
Pro Leu Arg Asp Leu Gly Gly Asp Leu Pro Leu Gln Ile Leu Pro His
 65                  70                  75                  80

Leu Asn Gly Pro Leu His Leu Ala Pro Met Thr Leu Arg Cys Thr Val
             85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
130                 135                 140

Leu Met Gly Leu Cys Asp Glu Thr Ala Thr Ile Phe Arg Glu Ile Thr
145                 150                 155                 160

Gly Tyr Asp Arg Val Met Val Tyr Arg Phe Asp Glu Glu Gly His Gly
                165                 170                 175

Glu Val Leu Ser Glu Arg Arg Arg Ala Asp Leu Glu Ala Phe Leu Gly
            180                 185                 190

Asn Arg Tyr Pro Ala Ser Thr Ile Pro Gln Ile Ala Arg Arg Leu Tyr
        195                 200                 205

Glu His Asn Arg Val Arg Leu Leu Val Asp Val Asn Tyr Thr Pro Val
210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Ile His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Ala Glu Thr Cys
290                 295                 300

Ala Ile Arg Ile Ala Ala Leu Glu Ser Phe Ala Gln Ser Gln Ser Lys
305                 310                 315                 320

<210> SEQ ID NO 6
<211> LENGTH: 960
<212> TYPE: DNA
<213> ORGANISM: Artificial Sequence
<220> FEATURE:
<223> OTHER INFORMATION: BrIFPv2, nucleic acid sequence

<400> SEQUENCE: 6
atgtcggtac cgctgactac ctcggcattc ggccacgcga ctctggctaa ctgtgaacgc      60
gagcagatcc acctggcggg ctccattcag ccgcacggta tcctgctggc tgtgaaagag     120
ccggacaacg tggtgatcca ggcttctatt aacgctgcgg agttcctgaa caccaactct     180
gttgttggcc gtccgctgcg tgacctgggc ggcgatctgc ctctgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gcctgatcgt agaactggaa     360
ccggcaacca agaccactaa cattgcgccg gctctggacg gtgcgtttca tcgtatcact     420
tcttcctcct ccctgatggg cctgtgtgac gaaaccgcga ctattttccg tgagattact     480
ggctacgacc gtgtgatggt ataccgtttc gatgaagagg gtcatggcga agtgctgtcc     540
gaacgtcgtc gtgcggacct ggaagcgttc ctgggtaacc gctaccccgg cgtctactatt     600
```

```
ccgcagatcg ctcgtcgcct gtacgaacat aaccgtgttc gcctgctggt agatgtgaac    660
tatactccgg ttccgctgca gccgcgcatc agcccgctga acggtcgtga cctggatatg    720
tccctgtctt gcctgcgctc tatgtccccg atccaccaga aatacatgca ggacatgggc    780
gttggcgcga ccctggtttg ctctctgatg gtgtctggtc gtctgtgggg tctgatcgct    840
tgccaccact acgaaccgcg cttcgttccg ttccacattc gcgctgctgg cgaagcgctg    900
gcggaaactt gtgcgatccg catcgcggcg ctggagagct ttgcacagtc tcagtccaaa    960
```

<210> SEQ ID NO 7
<211> LENGTH: 320
<212> TYPE: PRT
<213> ORGANISM: Artificial Sequence
<220> FEATURE:
<223> OTHER INFORMATION: BrIFPv3, amino acid sequence

<400> SEQUENCE: 7

```
Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asp Glu Thr Ala Thr Ile Ile Arg Glu Ile Thr
145                 150                 155                 160

Gly Tyr Asp Arg Val Met Val Tyr Arg Phe Asp Glu Glu Gly Asn Gly
                165                 170                 175

Glu Val Leu Ser Glu Arg Arg Arg Ala Asp Leu Glu Ala Phe Leu Gly
            180                 185                 190

Asn Arg Tyr Pro Ala Ser Thr Ile Pro Gln Ile Ala Arg Arg Leu Tyr
        195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Ile His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Ala Glu Thr Cys
    290                 295                 300
```

Ala Ile Arg Ile Ala Thr Leu Glu Ser Phe Ala Gln Ser Gln Ser Lys
305                 310                 315                 320

<210> SEQ ID NO 8
<211> LENGTH: 960
<212> TYPE: DNA
<213> ORGANISM: Artificial Sequence
<220> FEATURE:
<223> OTHER INFORMATION: BrIFPv3, nucleic acid sequence

<400> SEQUENCE: 8

```
atgtcggtac cgctgactac ctcagcattc ggccacgcgt ttctggctaa ctgtgaacgc      60
gagcagatcc acctggcggg ctccattcag ccgcacggta cctgctggc tgtgaaagag      120
ccggacaacg tggtgatcca ggcttctatt aacgctgcgg agttcctgaa caccaactct     180
gttgttggcc gtccgctgcg tgacctgggc ggcgatctgc ctttgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gctgatcgt agaactggaa      360
ccagcaacca agaccactaa cattgcgccg gctctggacg gtgcgtttca tcgtatcact     420
tcttcatcct ccctgatggg cctgtgtgac gaaaccgcga ctattatccg tgagattact     480
ggctacgacc gtgtgatggt ataccgtttc gatgaagagg gtaatggcga agtgctgtcc    540
gaacgtcgtc gtgcggacct ggaagcgttc ctgggtaacc gctacccggc gtctactatt    600
ccgcagatcg ctcgtcgcct gtacgaacat aaccgtgttc gcctgctggt agatgtgaac    660
tatactccgg ttccgctaca gccgcgcatc agcccgctga acggtcgtga tctggatatg    720
tccctgtctt gcctgcgctc tatgtccccg atccaccaga atacatgca ggacatgggc    780
gttggcgcga ccctggtttg ctctctgatg gtgtctggtc gtctgtgggg tctgatcgct    840
tgccaccact acgaaccgcg cttcgttccg ttccacattc gcgctgctgg cgaagcgctg   900
gcggaaactt gtgcgatccg catcgcgacg ctggagagct ttgcacagtc tcagtccaaa   960
```

<210> SEQ ID NO 9
<211> LENGTH: 960
<212> TYPE: DNA
<213> ORGANISM: Artificial Sequence
<220> FEATURE:
<223> OTHER INFORMATION: iBlueberry: mIFP/I251C, nucleic acid sequence

<400> SEQUENCE: 9

```
atgtcggtac cgctgactac ctcagcattc ggccacgcgt ttctggctaa ctgtgaacgc      60
gagcagatcc acctggcggg ctccattcag ccgcacggta cctgctggc tgtgaaagag      120
ccggacaacg tggtgatcca ggcttctatt aacgctgcgg agttcctgaa caccaactct     180
gttgttggcc gtccgctgcg tgacctgggc ggcgatctgc ctttgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gctgatcgt agaactggaa      360
ccagcaacca agaccactaa cattgcgccg gctctggacg gtgcgtttca tcgtatcact     420
tcttcatcct ccctgatggg cctgtgtgac gaaaccgcga ctattatccg tgagattact     480
ggctacgacc gtgtgatggt agtacgtttc gatgaagagg gtaatggcga aattctgtcc    540
gaacgtcgtc gtgcggacct ggaagcgttc ctgggtaacc gctacccggc gtctactatt    600
ccgcagatcg ctcgtcgcct gtacgaacat aaccgtgttc gcctgctggt agatgtgaac    660
tatactccgg ttccgctaca gccgcgcatc agcccgctga acggtcgtga tctggatatg    720
```

```
tccctgtctt gcctgcgctc tatgtccccg tgccaccaga atacatgca ggacatgggc    780 gttggcgcga ccctggtttg ctctctgatg gtgtctggtc gtctgtgggg tctgatcgct    840
tgccaccact acgaaccgcg cttcgttccg ttccacattc gcgctgctgg cgaagcgctg    900
gcggaaactt gtgcgatccg catcgcgacg ctggagagct ttgcacagtc tcagtccaaa    960
```

<210> SEQ ID NO 10
<211> LENGTH: 320
<212> TYPE: PRT
<213> ORGANISM: Artificial Sequence
<220> FEATURE:
<223> OTHER INFORMATION: iBlueberry: mIFP/I251C, amino acid sequence

<400> SEQUENCE: 10

```
Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
                20                  25                  30

Gly Ile Leu Leu Ala Val Lys Glu Pro Asp Asn Val Val Ile Gln Ala
            35                  40                  45

Ser Ile Asn Ala Ala Glu Phe Leu Asn Thr Asn Ser Val Val Gly Arg
        50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
130                 135                 140

Leu Met Gly Leu Cys Asp Glu Thr Ala Thr Ile Ile Arg Glu Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Arg Ala Asp Leu Glu Ala Phe Leu Gly
            180                 185                 190

Asn Arg Tyr Pro Ala Ser Thr Ile Pro Gln Ile Ala Arg Arg Leu Tyr
        195                 200                 205

Glu His Asn Arg Val Arg Leu Leu Val Asp Val Asn Tyr Thr Pro Val
210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Glu Thr Cys
290                 295                 300

Ala Ile Arg Ile Ala Thr Leu Glu Ser Phe Ala Gln Ser Gln Ser Lys
305                 310                 315                 320
```

<210> SEQ ID NO 11
<211> LENGTH: 960
<212> TYPE: DNA
<213> ORGANISM: Artificial Sequence
<220> FEATURE:
<223> OTHER INFORMATION: iBlueberry1.1, nucleic acid sequence

<400> SEQUENCE: 11

```
atgtcggtac cgctgactac ctcagcattc ggccacgcgt ttctggctaa ctgtgaacgc    60
gagcagatcc acctggcggg ctccattcag ccgcacggta cctgctggc tgtgaaagag   120
ccggacaacg tggtgatcca ggcttctatt aacgctgcgg agttcctgaa caccaactct   180
gttgttggcc gtccgctgcg tgacctgggc ggcgatctgc ctttgcagat cctgccgcac   240
ctgaacggcc cgctgcacct ggctccgatg accctgcgtt gtaccgtggg ttctccgccg   300
cgtcgtgtgg actgtaccat tcatcgtccg tctaacggcg gcctgatcgt agaactggaa   360
ccagcaacca agaccactaa cattgcgccg gctctggacg gtgcgtttca tcgtatcact   420
tcttcatcct ccctgatggg cctgtgtgac gaaaccgcga ctattatccg tgtgattact   480
ggctacgacc gtgtgatggt agtacgtttc gatgaagagg gtaatggcga aattctgtcc   540
gaacgtcgtc gttcggacct ggaagcgttc ctgggtaacc gctacccggc gtctactatt   600
ccgcagaacg ctcgtcgcct gtacgaacat aaccgtgttc gcctgctggt agatgtgaac   660
tatactccgg ttccgctaca gccgcgcatc agcccgctga acggtcgtga tctggatatg   720
tccctgtctt gcctgcgctc tatgtccccg tgccaccaga aatatatgca ggacatgggc   780
gttggcgcga ccctggtttg ctctctgatg gtgtcaggtc gtctgtgggg tctgatcgct   840
tgccaccact acgaaccgcg cttcgttccg ttccacattc gcgctgctgg cgaagccctg   900
gcggaaactt gtgcgatccg catcgcgacg ctggagagct ttgcacagtc tcagtccaaa   960
```

<210> SEQ ID NO 12
<211> LENGTH: 320
<212> TYPE: PRT
<213> ORGANISM: Artificial Sequence
<220> FEATURE:
<223> OTHER INFORMATION: iBlueberry1.1, amino acid sequence

<400> SEQUENCE: 12

```
Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asp Glu Thr Ala Thr Ile Ile Arg Val Ile Thr
```

145                 150                 155                 160
Gly Tyr Asp Arg Val Met Val Arg Phe Asp Glu Glu Gly Asn Gly
                    165                 170                 175

Glu Ile Leu Ser Glu Arg Arg Arg Ser Asp Leu Glu Ala Phe Leu Gly
                180                 185                 190

Asn Arg Tyr Pro Ala Ser Thr Ile Pro Gln Asn Ala Arg Arg Leu Tyr
                195                 200                 205

Glu His Asn Arg Val Arg Leu Leu Val Asp Val Asn Tyr Thr Pro Val
            210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                    245                 250                 255

Gln Asp Met Gly Val Gly Ala Thr Leu Val Cys Ser Leu Met Val Ser
                260                 265                 270

Gly Arg Leu Trp Gly Leu Ile Ala Cys His His Tyr Glu Pro Arg Phe
            275                 280                 285

Val Pro Phe His Ile Arg Ala Ala Gly Glu Ala Leu Ala Glu Thr Cys
        290                 295                 300

Ala Ile Arg Ile Ala Thr Leu Glu Ser Phe Ala Gln Ser Gln Ser Lys
305                 310                 315                 320

<210> SEQ ID NO 13
<211> LENGTH: 960
<212> TYPE: DNA
<213> ORGANISM: Artificial Sequence
<220> FEATURE:
<223> OTHER INFORMATION: iBlueberry1.2, nucleic acid sequence

<400> SEQUENCE: 13
atgtcggtac cgctgactac ctcagcatac ggccacgcgt ttctggctaa ctgtgaacgc      60
gagcagatcc acctggcggg ctccattcag ccgcacggta cctgctggc tgtgaaagag     120 ccggacaacg tggtgatcca ggcttctatt aacgctgcgg agttcctgaa caccaactct     180
gttgttgacc gtccgctgcg tgacctgggc ggcgatctgc ctttgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gcctgatcgt agaactggaa     360
ccagcaacca agaccactaa cattgcgccg gctctggacg gtgcgtttca tcgtatcact     420
tcttcatcct ccctgatggg cctgtgtaac gaaaccgcga ctattatccg tgagattact     480
ggctacgacc gtgtgatggt agtacgtttc gatgaagagg gtaatggcga aattctgtcc     540
gaacgtcgtc gtgcggacct ggaagcgtta ctgggtaacc gctacccggc gtctactatt     600
ccgcagatcg ctcgtcgcct gtacgaacat aaccgtgttc gcctgctggt agatgtgaac     660
tatactccgg ttccgctaca gccgcgcatc agcccgctga acggtcgtga tctggatatg     720
tccctgtctt gcctgcgctc tatgtccccg tgccaccaga aatacatgca ggacatgggc     780
gttggcgcga ccctggtttg ctctctgatg gtgtctggtc gtctgtgggg tctgatcgct     840
tgccaccact acgaaccgcg cttcgttccg ttccacattc gcgctgctgg cgaagcgctg     900
gcggaaactt gtgcgatccg catcgcgacg ctggagagct tgcacagtc tcagtccaaa     960

<210> SEQ ID NO 14
<211> LENGTH: 320
<212> TYPE: PRT
<213> ORGANISM: Artificial Sequence
<220> FEATURE:
<223> OTHER INFORMATION: iBlueberry1.2, amino acid sequence

<400> SEQUENCE: 14

Met Ser Val Pro Leu Thr Thr Ser Ala Tyr Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Asp Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asn Glu Thr Ala Thr Ile Ile Arg Glu Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Arg Ala Asp Leu Glu Ala Leu Leu Gly
            180                 185                 190

Asn Arg Tyr Pro Ala Ser Thr Ile Pro Gln Ile Ala Arg Arg Leu Tyr
        195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Ala Glu Thr Cys
    290                 295                 300

Ala Ile Arg Ile Ala Thr Leu Glu Ser Phe Ala Gln Ser Gln Ser Lys
305                 310                 315                 320

<210> SEQ ID NO 15
<211> LENGTH: 960
<212> TYPE: DNA
<213> ORGANISM: Artificial Sequence
<220> FEATURE:
<223> OTHER INFORMATION: iBlueberry2.1, nucleic acid sequence

<400> SEQUENCE: 15
atgtcggtac cgctgactac ctcagcatac ggccacgcgt ttctggctaa ctgtgaacgc     60
gagcagatcc acctggcggg ctccattcag ccgcacggta tcctgctggc tgtgaaagag    120

```
ccggacaacg tggtgatcca ggcttctatt aacgctgcgg agttcctgaa taccaactct    180
gttgttgacc gtccgctgcg tgacctgggc ggcgatctgc ctttgcagat cctgccgcac    240
ctgaacggcc cgctgcacct ggctccgatg acactgcgtt gtaccgtggg ttctccgccg    300
cgtcgtgtgg actgtaccat tcatcgtccg tctaacggcg gcctgatcgt agaactggaa    360
ccagcaacca agaccactaa cattgcgccg gctctggacg gtgcgtttca tcgtatcact    420
tcttcatcct ccctgatggg cctgtgtaac gaaaccgcga ctattatccg tgagattact    480
ggctacgacc gtgtgatggt agtacgtttc gatgaagagg gtaatggcga aattctgtcc    540
gaacgtcgtc gttcggacct ggaagcgttc ctgggtaacc gctaccctgc gtctactatt    600
ccacagaacg ctcgtcgcct gtacgaacat aaccgtcttc gcctgctggt agatgtgaac    660
tatactccgg ttccgctaca gccgcgcatc agcccgctga acggtcgtga tctggatatg    720
tccctgtctt gcctgcgctc tatgtccccg tgccaccaga aatatatgca ggacatgggc    780
gttggcgcga ccctggtttg ctctctgatg gtgtcaggtc gtctgtgggg tctgatcgct    840
tgccaccact acgaaccgcg cttcgttccg ttccacattc gcgctgctgg cgaagccctg    900
gcggaaactt gtgcgatccg catcgcgacg ctggagagct ttgcacagtc tcagtccaaa    960
```

<210> SEQ ID NO 16
<211> LENGTH: 320
<212> TYPE: PRT
<213> ORGANISM: Artificial Sequence
<220> FEATURE:
<223> OTHER INFORMATION: iBlueberry2.1, amino acid sequence

<400> SEQUENCE: 16

Met Ser Val Pro Leu Thr Thr Ser Ala Tyr Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Asp Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asn Glu Thr Ala Thr Ile Ile Arg Glu Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Ser Asp Leu Glu Ala Phe Leu Gly
            180                 185                 190

Asn Arg Tyr Pro Ala Ser Thr Ile Pro Gln Asn Ala Arg Arg Leu Tyr
        195                 200                 205

Glu His Asn Arg Leu Arg Leu Leu Val Asp Val Asn Tyr Thr Pro Val
    210                 215                 220

```
Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
            245                 250                 255

Gln Asp Met Gly Val Gly Ala Thr Leu Val Cys Ser Leu Met Val Ser
        260                 265                 270

Gly Arg Leu Trp Gly Leu Ile Ala Cys His His Tyr Glu Pro Arg Phe
    275                 280                 285

Val Pro Phe His Ile Arg Ala Ala Gly Glu Ala Leu Ala Glu Thr Cys
290                 295                 300

Ala Ile Arg Ile Ala Thr Leu Glu Ser Phe Ala Gln Ser Gln Ser Lys
305                 310                 315                 320

<210> SEQ ID NO 17
<211> LENGTH: 960
<212> TYPE: DNA
<213> ORGANISM: Artificial Sequence
<220> FEATURE:
<223> OTHER INFORMATION: iBlueberry2.2, nucleic acid sequence

<400> SEQUENCE: 17
atgtcggtac cgctgactac ctcagcattc ggccacgcgt ttctggctaa ctgtgaacgc     60
gagcagatcc acctggcggg ctccattcag ccgcacggta cctgctggc tgtgaaagag    120 ccggacaacg tggtgatcca ggcttctatt aacgctgcgg agttcctgaa caccaactct    180
gttgttggcc gtccgctgcg tgacctgggc ggcgatctgc ttttgcagat cctgccgcac    240
ctgaacggcc cgctgcacct ggctccgatg accctgcgtt gtaccgtggg ttctccgccg    300
cgtcgtgtgg actgtaccat tcatcgtccg tctaacggcg gcctgatcgt agaactggaa    360
ccagcaacca agaccactaa cattgcgccg gctctggacg gtgcgtttca tcgtatcact    420
tcttcatcct ccctgatggg cctgtgtgac gaaaccgcga ctattatccg tgtgattact    480
ggctacgacc gtgtgatggt agtacgtttc gatgaagagg gtaatggcga aattctgtcc    540
gaacgtcgtc gttcggacct ggaagcgttc ctgggtaacc gctacccggc gtctactatt    600
ccgcagaacg ctcgtcgcct gtacgaacat aaccgtgttc gcctgctggt agatgtgaac    660
tatactccgg ttccgctaca gccgcgcatc agcccgctga acggtcgtga tctggatatg    720
tccctgtctt gcctgcgctc tatgtccccg tgccaccaga aatatatgca ggacatgggc    780
gttggcgcga ccctggtttg ctctctgatg gtgtcaggtc gtctgtgggg tctgatcgct    840
tgccaccact acgaaccgcg cttcgttccg ttccacattc gcgctgctgg cgaagccctg    900
gcggaaactt gtgcgatccg catcgcgacg ctggagagct ttgcacagtc tcagtcctaa    960

<210> SEQ ID NO 18
<211> LENGTH: 319
<212> TYPE: PRT
<213> ORGANISM: Artificial Sequence
<220> FEATURE:
<223> OTHER INFORMATION: iBlueberry2.2, amino acid sequence

<400> SEQUENCE: 18

Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45
```

| Ser | Ile | Asn | Ala | Ala | Glu | Phe | Leu | Asn | Thr | Asn | Ser | Val | Val | Gly | Arg |
| --- | --- | --- | --- | --- | --- | --- | --- | --- | --- | --- | --- | --- | --- | --- | --- |
| | 50 | | | | 55 | | | | | 60 | | | | | |

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asp Glu Thr Ala Thr Ile Ile Arg Val Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Ser Asp Leu Glu Ala Phe Leu Gly
            180                 185                 190

Asn Arg Tyr Pro Ala Ser Thr Ile Pro Gln Asn Ala Arg Arg Leu Tyr
        195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Ala Glu Thr Cys
    290                 295                 300

Ala Ile Arg Ile Ala Thr Leu Glu Ser Phe Ala Gln Ser Gln Ser
305                 310                 315

<210> SEQ ID NO 19
<211> LENGTH: 960
<212> TYPE: DNA
<213> ORGANISM: Artificial Sequence
<220> FEATURE:
<223> OTHER INFORMATION: iBlueberry2.3, nucleic acid sequence

<400> SEQUENCE: 19

```
atgtcggtac cgctgactac ctcagcatac ggccacgagt ttctggctaa ctgtgaacgc      60
gagcagatcc acctggcggg ctccattcag ccgcacggta tcctgctggc tgtgaaagag     120
ccggacaacg tggtgatcca ggcttctatt aacgctgcgg agttcctgaa caccaactct     180
gttgttgacc gtccgctgcg tgacctgggc ggcgatctgc ctttgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gcctgatcgt agaactggaa     360
ccagcaacca agaccactaa catagcgccg ctctctggacg tgcgttttca tcgtatcaca     420
tcttcatcct ccctgatggg cctgtgtaac gaaaccgcga ctattatccg tgagattact     480
ggctacgacc gtgtgatggt agtacgtttc gatgaagagg gtaatggcga aattctgtcc     540
```

```
gaacgtcgtc gttcggacct ggaagcgttc ctgggtaacc gctacccggc gtctactatt    600
ccgcagaacg ctcgtcgcct gtacgaacat aaccgtgttc gcctgctggt agatgtgaac    660
tatactccgg ttccgctaca gccgcgcatc agcccgctga acggtcgtga tctggatatg    720
tccctgtctt gcctgcgctc tatgtccccg taccaccaga aatatatgca ggacatgggc    780
attggcgcga ccctggtttg ctctctgatg gtgtcaggtc gtctgtgggg tctgatcgct    840
tgccaccact acgaaccgcg cttcgttccg ttccacattc gcgctgctgg cgaagccctg    900
gcggaaactt gtgcgatccg catcgcgacg ctggggagct ttgcatagtc tcagtccaaa    960
```

<210> SEQ ID NO 20
<211> LENGTH: 315
<212> TYPE: PRT
<213> ORGANISM: Artificial Sequence
<220> FEATURE:
<223> OTHER INFORMATION: iBlueberry2.3, amino acid sequence

<400> SEQUENCE: 20

```
Met Ser Val Pro Leu Thr Thr Ser Ala Tyr Gly His Glu Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Asp Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asn Glu Thr Ala Thr Ile Ile Arg Glu Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Arg Ser Asp Leu Glu Ala Phe Leu Gly
            180                 185                 190

Asn Arg Tyr Pro Ala Ser Thr Ile Pro Gln Asn Ala Arg Arg Leu Tyr
        195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Tyr His Gln Lys Tyr Met
                245                 250                 255

Gln Asp Met Gly Ile Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285
```

```
Val Pro Phe His Ile Arg Ala Ala Gly Glu Ala Leu Ala Glu Thr Cys
        290                 295                 300

Ala Ile Arg Ile Ala Thr Leu Gly Ser Phe Ala
305                 310                 315

<210> SEQ ID NO 21
<211> LENGTH: 960
<212> TYPE: DNA
<213> ORGANISM: Artificial Sequence
<220> FEATURE:
<223> OTHER INFORMATION: iBlueberry2.4, nucleic acid sequence

<400> SEQUENCE: 21
atgtcggtac cgctgactac ctcagcattc ggccacgcgt ttctggctaa ctgtgaacgc      60
gagcagatcc acctggcggg ctccattcag ccgcacggta tcctgctggc tgtgaaagag     120
ccggacaacg tggtgatcca ggcttctatt aacgctgcgg agttcctgaa caccaactct     180
gttgttggcc gtccgctgcg tgacctgggc ggcgatctgc ctttgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gcctgatcgt agaactggaa     360
ccagcaacca agaccactaa cattgcgccg gctctgacg gtgcgtttca tcgtatcact      420
tcttcatcct ccctgatggg cctgtgtgac gaaaccgcga ctattatccg tgtgattact     480
ggctacgacc gtgttatggt agtacgtttc gatgaagagg gtaatggcga attctgtcc      540 gaacgtcgtc gtgcggacct ggaagcgtta ctgggtaacc gctacccggc gtctacaatt     600
ccgcagatcg ctcgtcgcct gtacgaacat aaccgtgttc gctgctggt agatgtgaac      660 tatactccgg ttccgctgga gccgcgcatc agcccgctga acggtcgtga tctggatatg     720
tccctgtctt gcctgcgctc tatgtccccg tgccaccaga aatacatgca ggacatgggc     780
gttggcgcga ccctggtttg ctctctgatg gtgtctggtc gtctgtgggg tctgatcgct     840
tgccaccact acgaaccgcg cttcgttccg ttccacattc gcgctgctgg cgaagcgctg     900
gcggaaactt gtgcgatccg catcgcgacg ctggagagct ttgcacagtc tcagtccaaa    960

<210> SEQ ID NO 22
<211> LENGTH: 320
<212> TYPE: PRT
<213> ORGANISM: Artificial Sequence
<220> FEATURE:
<223> OTHER INFORMATION: iBlueberry2.4, amino acid sequence

<400> SEQUENCE: 22

Met Ser Val Pro Leu Thr Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110
```

```
Gly Gly Leu Ile Val Glu Leu Glu Pro Ala Thr Lys Thr Thr Asn Ile
            115                 120                 125

Ala Pro Ala Leu Asp Gly Ala Phe His Arg Ile Thr Ser Ser Ser Ser
130                 135                 140

Leu Met Gly Leu Cys Asp Glu Thr Ala Thr Ile Ile Arg Val Ile Thr
145                 150                 155                 160

Gly Tyr Asp Arg Val Met Val Val Arg Phe Asp Glu Gly Asn Gly
                165                 170                 175

Glu Ile Leu Ser Glu Arg Arg Ala Asp Leu Glu Ala Leu Leu Gly
            180                 185                 190

Asn Arg Tyr Pro Ala Ser Thr Ile Pro Gln Ile Ala Arg Arg Leu Tyr
            195                 200                 205

Glu His Asn Arg Val Arg Leu Leu Val Asp Val Asn Tyr Thr Pro Val
            210                 215                 220

Pro Leu Glu Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
            275                 280                 285

Val Pro Phe His Ile Arg Ala Ala Gly Glu Ala Leu Ala Glu Thr Cys
            290                 295                 300

Ala Ile Arg Ile Ala Thr Leu Glu Ser Phe Ala Gln Ser Gln Ser Lys
305                 310                 315                 320

<210> SEQ ID NO 23
<211> LENGTH: 960
<212> TYPE: DNA
<213> ORGANISM: Artificial Sequence
<220> FEATURE:
<223> OTHER INFORMATION: iBlueberry2.5, nucleic acid sequence

<400> SEQUENCE: 23
atgtcggtac cgctgattac ctcagcattc ggccacgcgt ttctggctaa ctgtgaacgc      60
gagcagatcc acctggcggg ctccattcag ccgcacggta tcctgctggc tgtgaaagag     120
ccggataacg tggtgatcca ggcttctatt aacgctgcgg agttcctgaa caccaactct     180
gttgttggcc gtccgctgcg tgacctgggc ggcgatctgc ctttgcagat cctgccgcac     240
ctgaacggcc cgctgcacct ggctccgatg accctgcgtt gtaccgtggg ttctccgccg     300
cgtcgtgtgg actgtaccat tcatcgtccg tctaacggcg gcctgatcgt agaactggaa     360
ccagcaacca agaccactaa cattgcgccg gctctggacg tgcgtttca tcgtatcact     420 tcttcatcct ccctgatggg cctgtgtgac gaaaccgcga ctattatccg tgtgattact     480
ggctacgacc gtgtgatggt agtacgtttc gatgaagagg gtaatggcga attctgtcc      540 gaacgtcgtc gtgcggacct ggaagcgtta ctgggtaacc gctaccggc gtctactatt      600 ccgcagatcg ctcgtcgcct gtacgaacat aaccgtgttc gcctgctggt agatgtgaac     660
tatactccgg ttccgctaca gccgcgcatc agcccgctga cggtcgtga tctggatatg      720 tccctgtctt gctgcgctc tatgtccccg tgccaccaga atacatgca ggacatgggc      780 gttggcgcga ccctggtttg ctctctgatg gtgtctggtc gtctgtgggg tctgatcgct     840
tgccaccact acgaaccgcg cttcgttccg ttccacattc gcgctgctgg cgaagcgctg     900
```
gcggaaactt gtgcgatccg catcgcgacg ctggagagct ttgcacagtc tcagtccaaa    960

<210> SEQ ID NO 24
<211> LENGTH: 320
<212> TYPE: PRT
<213> ORGANISM: Artificial Sequence
<220> FEATURE:
<223> OTHER INFORMATION: iBlueberry2.5, amino acid sequence

<400> SEQUENCE: 24

Met Ser Val Pro Leu Ile Thr Ser Ala Phe Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Gly Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asp Glu Thr Ala Thr Ile Ile Arg Val Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Ala Asp Leu Glu Ala Leu Leu Gly
            180                 185                 190

Asn Arg Tyr Pro Ala Ser Thr Ile Pro Gln Ile Ala Arg Arg Leu Tyr
        195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                245                 250                 255

Gln Asp Met Gly Val Gly Ala Thr Leu Val Cys Ser Leu Met Val Ser
            260                 265                 270

Gly Arg Leu Trp Gly Leu Ile Ala Cys His His Tyr Glu Pro Arg Phe
        275                 280                 285

Val Pro Phe His Ile Arg Ala Ala Gly Glu Ala Leu Ala Glu Thr Cys
    290                 295                 300

Ala Ile Arg Ile Ala Thr Leu Glu Ser Phe Ala Gln Ser Gln Ser Lys
305                 310                 315                 320

<210> SEQ ID NO 25
<211> LENGTH: 960
<212> TYPE: DNA
<213> ORGANISM: Artificial Sequence
<220> FEATURE:
<223> OTHER INFORMATION: iBlueberry2.6, nucleic acid sequence

<400> SEQUENCE: 25

```
atgtcggtac cgctgactac ctcagcatac ggccacgcgt ttctggctaa ctgtgaacgc    60
gagcagatcc acctggcggg ctccattcag ccgcacggta tcctgctggc tgtgaaagag   120
ccggacaacg tggtgatcca ggcttctatt aacgctgcgg agttcctgaa caccaactct   180
gttgttgacc gtccgctgcg tgacctgggc ggcgatctgc ctttgcagat cctgccgcac   240
ctgaacggtc cgctgcacct ggctccgatg accctgcgtt gtaccgtggg ttctccgccg   300
cgtcgtgtgg actgtaccat tcatcgtccg tctaacggcg gcctgatcgt agaactggaa   360
ccagcaacca agaccactaa cattgcgccg gctctggacg gtgcgtttca tcgtatcact   420
tcttcatcct ccctgatggg cctgtgtgac gaaaccgcga ctattatccg tgtgattact   480
ggctacgacc gtgtgatggt agtacgtttc gatgaagagg gtaatggcga aattctgtcc   540
gaacgtcgtc gttcggacct ggaagcgttc ctgggtaacc gctacccggc gtctactatt   600
ccgcagaacg ctcgtcgcct gtacgaacat aaccgtgttc gcctgctggt agatgtgaac   660
tatactccgg ttccgctaca accgcgcatc agcccgctga acggtcgtga tctggatatg   720
tccctgtctt gcctgcgctc tatgtccccg tgccaccaga aatatatgca ggacatgggc   780
gttggcgcga ccctggtttg ctctctgatg gtgtcaggtc gtctgtgggg tctgatcgct   840
tgccaccact acgaaccgcg cttcgttccg ttccacattc gcgctgctgg tgaagccctg   900
gcggaaactt gtgcgatccg catcgcgacg ctggagagct ttgcacagtc tcagtccaaa   960
```

<210> SEQ ID NO 26
<211> LENGTH: 320
<212> TYPE: PRT
<213> ORGANISM: Artificial Sequence
<220> FEATURE:
<223> OTHER INFORMATION: iBlueberry2.6, amino acid sequence

<400> SEQUENCE: 26

```
Met Ser Val Pro Leu Thr Thr Ser Ala Tyr Gly His Ala Phe Leu Ala
1               5                   10                  15

Asn Cys Glu Arg Glu Gln Ile His Leu Ala Gly Ser Ile Gln Pro His
            20                  25                  30

Gly Ile Leu Leu Ala Val Lys Glu Pro Asp Asn Val Val Ile Gln Ala
        35                  40                  45

Ser Ile Asn Ala Ala Glu Phe Leu Asn Thr Asn Ser Val Val Asp Arg
    50                  55                  60

Pro Leu Arg Asp Leu Gly Gly Asp Leu Pro Leu Gln Ile Leu Pro His
65                  70                  75                  80

Leu Asn Gly Pro Leu His Leu Ala Pro Met Thr Leu Arg Cys Thr Val
                85                  90                  95

Gly Ser Pro Pro Arg Arg Val Asp Cys Thr Ile His Arg Pro Ser Asn
            100                 105                 110

Gly Gly Leu Ile Val Glu Leu Glu Pro Ala Thr Lys Thr Thr Asn Ile
        115                 120                 125

Ala Pro Ala Leu Asp Gly Ala Phe His Arg Ile Thr Ser Ser Ser Ser
    130                 135                 140

Leu Met Gly Leu Cys Asp Glu Thr Ala Thr Ile Ile Arg Val Ile Thr
145                 150                 155                 160

Gly Tyr Asp Arg Val Met Val Val Arg Phe Asp Glu Glu Gly Asn Gly
                165                 170                 175

Glu Ile Leu Ser Glu Arg Arg Arg Ser Asp Leu Glu Ala Phe Leu Gly
```

-continued

```
                    180                 185                 190
Asn Arg Tyr Pro Ala Ser Thr Ile Pro Gln Asn Ala Arg Arg Leu Tyr
            195                 200                 205

Glu His Asn Arg Val Arg Leu Leu Val Asp Val Asn Tyr Thr Pro Val
    210                 215                 220

Pro Leu Gln Pro Arg Ile Ser Pro Leu Asn Gly Arg Asp Leu Asp Met
225                 230                 235                 240

Ser Leu Ser Cys Leu Arg Ser Met Ser Pro Cys His Gln Lys Tyr Met
                245                 250                 255

Gln Asp Met Gly Val Gly Ala Thr Leu Val Cys Ser Leu Met Val Ser
                260                 265                 270

Gly Arg Leu Trp Gly Leu Ile Ala Cys His His Tyr Glu Pro Arg Phe
            275                 280                 285

Val Pro Phe His Ile Arg Ala Ala Gly Glu Ala Leu Ala Glu Thr Cys
        290                 295                 300

Ala Ile Arg Ile Ala Thr Leu Glu Ser Phe Ala Gln Ser Gln Ser Lys
305                 310                 315                 320
```

MONOMERIC AND BRIGHT INFRARED FLUORESCENT PROTEINS

FIELD OF THE INVENTION

This invention relates to the discovery of novel infrared fluorescent proteins and methods of use thereof.

BACKGROUND OF THE INVENTION

The identification and isolation of fluorescent proteins in various organisms, including marine organisms, has provided a valuable tool to molecular biology. The isolated fluorescent proteins have been used in their natural state and have been modified to elicit excitation/emission shifts in order to maximize their utility in in vitro and in vivo imaging. Green Fluorescent Proteins (GFPs) are the most widely utilized of the fluorescent proteins.

GFPs are involved in bioluminescence in a variety of marine invertebrates, including jellyfish such as *Aequorea Victoria* (Morise, H., et al., Biochemistry 13:2656-2662 (1974); Prendergast, F. G., and Mann, K. G., Biochemistry 17:3448-3453 (1978); Ward, W. W., Photochem. Photobiol. Rev. 4:1-57 (1979) and the sea pansy *Renilla reniformis* (Ward, W. W., and Cormier, M. J., Photochem. Photobiol. 27:389-396 (1978); Ward, W. W., et al., Photochem. Photobiol. 31:611-615 (1980)). The GFP isolated from *A. victoria* has been cloned and the primary amino acid structure has been deduced. The chromophore of *A. victoria* GFP is a hexapeptide composed of amino acid residues 64-69 in which the amino acids at positions 65-67 (serine, tyrosine and glycine) form a heterocyclic ring (Prasher, D. C., et al., Gene 111:229-233 (1992); Cody, C. W., et al., Biochemistry 32:1212-1218 (1993)). Resolution of the crystal structure of GFP has shown that the chromophore is contained in a central α-helical region surrounded by an 11-stranded β-barrel (Ormo, M., et al., Science 273:1392-1395 (1996); Yang, F., et al., Nature Biotech. 14:1246-1251 (1996)). Upon purification, native GFP demonstrates an absorption maximum at 395 nm and an emission maximum at 509 nm (Morise, H., et al., Biochemistry 13:2656-2662 (1974); Ward, W. W., et al., Photochem. Photobiol. 31:611-615 (1980)) with exceptionally stable and virtually non-photobleaching fluorescence (Chalfie, M., et al., Science 263:802-805 (1994)).

GFP has been used as a fluorescent label in protein localization and conformation studies and has been used as a reporter gene in transfected prokaryotic and eukaryotic cells (Heim, R., et al., Proc. Natl. Acad. Sci. USA 91:1250-1254 (1994); Yokoe, H., and Meyer, T., Nature Biotech. 14:1252-1256 (1996); Chalfie, M., et al., Science 263:802-805 (1994); Wang, S., and Hazelrigg, T., Nature 369:400-403 (1994)). GFP has also been used in fluorescence resonance energy transfer studies of protein-protein interactions (Heim, R., and Tsien, R. Y., Curr. Biol. 6:178-182 (1996)). Since GFP is naturally fluorescent, exogenous substrates and cofactors are not necessary for induction of fluorescence. Furthermore, the GFP cDNA containing the complete coding region is less than 1 kb and is easily manipulated and inserted into a variety of vectors for use in creating stable transfectants (Chalfie, M., et al., Science 263:802-805 (1994)). However, despite the relative ease at expressing the GFPs, they offer limited use for in vivo imaging of whole animals (e.g., mice and humans) because of the low absorption/emission maxima (395 nm/509 nm).

Accordingly, although the availability of a wide variety of naturally occurring fluorescent proteins and spectral variants of the proteins has allowed for substantial advances, limitations to the use of fluorescent proteins remain. In particular, the use of fluorescent proteins in intact animals such as mice has been hindered by poor penetration of excitation light. For example, visibly fluorescent proteins have been cloned from jellyfish and corals and have revolutionized many areas of molecular and cell biology through in vivo expression, in vitro expression, protein labeling, and protein engineering; however, the use of such fluorescent proteins for imaging studies in intact animals (e.g., a mouse or human) is limited due to the excitation and emission maxima of the fluorescent proteins.

Specifically, the excitation and emission maxima of these fluorescent proteins generally do not exceeded 598 and 655 nm respectively (D. Shcherbo et al., Nat. Methods 4, 741 (2007); M. A. Shkrob et al., Biochem. J. 392, 649 (2005); L. Wang, W. C. Jackson, P. A. Steinbach, R. Y. Tsien, Proc. Natl. Acad. Sci. U.S.A. 101, 16745 (2004)). One exception are the phytochrome-based fluorescent proteins that have an excitation maximum of 644 nm and an emission maximum of 672 nm (A. J. Fischer, J. C. Lagarias, Proc. Natl. Acad. Sci. U.S.A. 101, 17334 (2004)). However, neither the traditional fluorescent protein cloned from marine animals or the phytochrom-based fluorescent proteins are well equipped for in vivo imaging in whole, living animals.

In vivo optical imaging of deep tissues in animals is most feasible between 650 and 900 nm because such wavelengths minimize the absorbance by hemoglobin, water, and lipids as well as light scattering (F. F. Jobsis, *Science* 198, 1264 (1977)); R. Weissleder and V. Ntziachristos, *Nat. Med.* 9, 123 (2003)). Accordingly, the emission maximum of 598 and the absorption maximum of 655 nm of traditional fluorescent proteins (e.g., fluorescent proteins cloned from jellyfish and corals) are ineffective at in vivo optical imaging of deep tissues in animals. Thus, genetically encoded, infrared fluorescent proteins (IFPs) are particularly valuable for whole-body imaging in cancer, stem cell biology, gene therapy, and other areas of biomedical research and treatment.

IFPs provide an orthogonal color to GFP in protein labeling. Unlike the previously described dimeric Bacterial Phytochrome Photoreceptors ("BphPs"), the monomeric IFPs described can be used effectively to label proteins. Furthermore, instructions for engineering such monomeric IFPs is described herein that are based on a structural analysis of the dimer interface, the identification of a naturally occurring monomeric BphP from a BphP sequence database, and the protein modification of the naturally occurring BphP into a monomeric IFP (mIFP). Using the methods described herein, novel blue-shifted mutant mIFPs (iBlueberry) were designed and made. Exemplary iBlueberry mIFPs were designed with single mutations that introduce new thioether bonds between the chromophore and the protein. This new bond creates a twist in the chromophore which decreases conjugation efficiency, resulting in ~40 nm blueshift. iBlueberry and mIFPs provide two orthogonal colors in protein labeling in cultured cells and model organisms and will find important applications in molecular and cell biology since biological processes such as cell signaling are carried out by many proteins forming dynamic network of protein-protein interactions.

BRIEF SUMMARY OF THE INVENTION

In various embodiments, the present invention provides a variant polypeptide of a parent polypeptide, wherein said variant polypeptide comprises at least 90% identity to SEQ ID NO:2. In another embodiment, the variant polypeptide comprises at least 95% identity to SEQ ID NO:2. In another embodiment, the variant polypeptide comprises SEQ ID NO: 2. In another embodiment, the variant polypeptide comprises the amino acid substitutions 2S, 8S, 14F, 74P, 107I, 128I, 146M, 156I, 168V, 175N, 178I, 185A, 199T, 210H, 256M, 258D, 292H, 310T, and 320K wherein the numbering of the amino acid positions correspond to that in native BrBphP from *Bradyrhizobium* sp. ORS278. In another embodiment, the present invention provides a fusion protein comprising the polypeptide.

In various embodiments, the present invention provides an isolated polynucleotide encoding a polypeptide comprising at least 90% identity to SEQ ID NO:2. In another embodiment, the polynucleotide comprises at least 95% identity to SEQ ID NO:2. In another embodiment, the polynucleotide comprises SEQ ID NO:2. In another embodiment, the variant polynucleotide encodes a polypeptide comprising the amino acid substitutions 2S, 8S, 14F, 74P, 107I, 128I, 146M, 156I, 168V, 175N, 178I, 185A, 199T, 210H, 256M, 258D, 292H, 310T, and 320K wherein the numbering of the amino acid positions correspond to that in native BrBphP from *Bradyrhizobium* sp. ORS278. In another embodiment, the present invention provides a vector comprising the polynucleotide. In another embodiment, the present invention provides a host cell comprising the vector. In another embodiment, the present invention provides a kit comprising the polynucleotide.

In various embodiments, the present invention provides a method of in vivo optical imaging, the method comprising the step of: expressing in a cell a polynucleotide encoding a first protein, the first protein comprising a variant polypeptide comprising at least 95% identity to SEQ ID NO:2.

In certain embodiments, the present invention provides a variant polypeptide of a parent polypeptide, wherein said variant polypeptide comprises at least 90% identity to SEQ ID NO:10. In certain embodiments, the variant polypeptide comprises at least 95% identity to SEQ ID NO:10. In certain embodiments, the variant polypeptide comprises SEQ ID NO:10. In certain embodiments, the variant polypeptide has the amino acid sequence selected from the group consisting of SEQ ID NOs:12, 14, 16, 18, 20, 22, 24, and 26. In certain embodiments, the variant polypeptide has the amino acid sequence of SEQ ID NO: 12. In certain embodiments, the variant polypeptide has the amino acid sequence of SEQ ID NO: 14.

In certain embodiments, the present invention provides an isolated polynucleotide encoding a polypeptide comprising at least 90% identity to SEQ ID NO:10. In certain embodiments the isolated polynucleotide comprises at least 95% identity to SEQ ID NO:10. In certain embodiments the isolated polynucleotide comprises SEQ ID NO:10. In certain embodiments the isolated polynucleotide has the amino acid sequence selected from the group consisting of SEQ ID NOs:12, 14, 16, 18, 20, 22, 24, and 26. In certain embodiments the isolated polynucleotide has the amino acid sequence of SEQ ID NO: 12. In certain embodiments the isolated polynucleotide has the amino acid sequence of SEQ ID NO: 14.

In certain embodiments, the present invention provides a vector comprising the polynucleotide sequence of any of claims 27-32.

In certain embodiments, the present invention provides a host cell comprising a vector comprising the polynucleotide sequence of any of claims 27-32.

In certain embodiments, the present invention provides a kit comprising an isolated polynucleotide encoding a polypeptide comprising at least 90% or 95% or 100% identity to SEQ ID NO:10. In certain embodiments, the present invention provides a kit comprising an isolated polynucleotide comprising an amino acid sequence selected from the group consisting of SEQ ID NOs:12, 14, 16, 18, 20, 22, 24, and 26.

In certain embodiments, the present invention provides a fusion protein comprising a polypeptide comprising at least 90% or 95% or 100% identity to SEQ ID NO:10. In certain embodiments, the present invention provides fusion protein comprising a polynucleotide comprising an amino acid sequence selected from the group consisting of SEQ ID NOs:12, 14, 16, 18, 20, 22, 24, and 26. In certain embodiments, the fusion protein has a fluorescence that is greater than 5-fold higher than IFP1.4. In certain embodiments, the fusion protein has a fluorescence that is greater than 10-fold higher than IFP1.4.

In certain embodiments, the present invention provides a method of in vivo optical imaging, the method comprising the step of: expressing in a cell a polynucleotide encoding a first protein, the first protein comprising a protein encoded by a polynucleotide comprising at least 90% or 95% or 100% identity to SEQ ID NO:10. In certain embodiments, the a method of in vivo optical imaging comprises a polynucleotide comprising an amino acid sequence selected from the group consisting of SEQ ID NOs:12, 14, 16, 18, 20, 22, 24, and 26. In certain embodiments, the cell is a bacterial or mammalian cell.

In certain embodiments, the present invention provides a method of detecting a cancer cell in vivo, the method comprising administering to a patient with cancer a fusion protein selected from any of the IFP-conjugates and fusion proteins described herein, wherein the fusion protein binds to a cancer cell, and detecting the fluorescence of the variant polypeptide. In specific embodiments the fusion protein is an antibody—variant polypeptide fusion protein (e.g., an antibody-IFP conjugate). In specific embodiments the fusion protein is a ligand—variant polypeptide fusion protein (e.g., a ligand-IFP conjugate). In specific embodiments, the ligand binds to EGFR.

In certain embodiments, the present invention provides a variant polypeptide of a parent polypeptide, wherein said variant polypeptide comprises at least 90% identity to SEQ ID NO:10. In certain embodiments, the variant polypeptide comprises at least 95% identity to SEQ ID NO:10. In certain embodiments, the variant polypeptide comprises SEQ ID NO:10. In certain embodiments, the variant polypeptide has the amino acid sequence selected from the group consisting of SEQ ID NOs:12, 14, 16, 18, 20, 22, 24, and 26. In certain embodiments, the variant polypeptide has the amino acid sequence of SEQ ID NO: 12. In certain embodiments, the variant polypeptide has the amino acid sequence of SEQ ID NO: 14.

In certain embodiments, the present invention provides an isolated polynucleotide encoding a polypeptide comprising at least 90% identity to SEQ ID NO:10. In certain embodiments the isolated polynucleotide comprises at least 95% identity to SEQ ID NO:10. In certain embodiments the isolated polynucleotide comprises SEQ ID NO:10. In certain embodiments the isolated polynucleotide has the amino acid sequence selected from the group consisting of SEQ ID NOs:12, 14, 16, 18, 20, 22, 24, and 26. In certain embodiments the isolated polynucleotide has the amino acid sequence of SEQ ID NO: 12. In certain embodiments the isolated polynucleotide has the amino acid sequence of SEQ ID NO: 14.

In certain embodiments, the present invention provides a vector comprising an isolated polynucleotide encoding a polypeptide comprising at least 90% identity to SEQ ID NO:10. In certain embodiments the present invention provides a vector comprising an isolated polynucleotide comprises at least 95% identity to SEQ ID NO:10. In certain embodiments the present invention provides a vector comprising an isolated polynucleotide comprises SEQ ID NO:10. In certain embodiments the present invention provides a vector comprising an isolated polynucleotide has the amino acid sequence selected from the group consisting of SEQ ID NOs:12, 14, 16, 18, 20, 22, 24, and 26. In certain embodiments the present invention provides a vector comprising an isolated polynucleotide has the amino acid sequence of SEQ ID NO: 12. In certain embodiments the present invention provides a vector comprising an isolated polynucleotide has the amino acid sequence of SEQ ID NO: 14.

In certain embodiments, the present invention provides a host cell comprising an isolated polynucleotide encoding a polypeptide comprising at least 90% identity to SEQ ID NO:10. In certain embodiments the present invention provides a host cell comprising an isolated polynucleotide comprises at least 95% identity to SEQ ID NO:10. In certain embodiments the present invention provides a host cell comprising an isolated polynucleotide comprises SEQ ID NO:10. In certain embodiments the present invention provides a host cell comprising an isolated polynucleotide has the amino acid sequence selected from the group consisting of SEQ ID NOs:12, 14, 16, 18, 20, 22, 24, and 26. In certain embodiments the present invention provides a host cell comprising an isolated polynucleotide has the amino acid sequence of SEQ ID NO: 12. In certain embodiments the present invention provides a host cell comprising an isolated polynucleotide has the amino acid sequence of SEQ ID NO: 14.

In certain embodiments, the present invention provides a kit comprising an isolated polynucleotide encoding a polypeptide comprising at least 90% identity to SEQ ID NO:10 wherein the isolated polynucleotide may optionally be incorporated into a vector and wherein the kit may optionally contain one or more cell lines.

In certain embodiments the present invention provides a kit comprising an isolated polynucleotide comprises at least 95% identity to SEQ ID NO:10 wherein the isolated polynucleotide may optionally be incorporated into a vector and wherein the kit may optionally contain one or more cell lines.

In certain embodiments the present invention provides a kit comprising an isolated polynucleotide comprises SEQ ID NO:10 wherein the isolated polynucleotide may optionally be incorporated into a vector and wherein the kit may optionally contain one or more cell lines.

In certain embodiments the present invention provides a kit comprising an isolated polynucleotide has the amino acid sequence selected from the group consisting of SEQ ID NOs:12, 14, 16, 18, 20, 22, 24, and 26 wherein the isolated polynucleotide may optionally be incorporated into a vector and wherein the kit may optionally contain one or more cell lines.

In certain embodiments the present invention provides a kit comprising an isolated polynucleotide has the amino acid sequence of SEQ ID NO: 12 wherein the isolated polynucleotide may optionally be incorporated into a vector and wherein the kit may optionally contain one or more cell lines.

In certain embodiments the present invention provides a kit comprising an isolated polynucleotide has the amino acid sequence of SEQ ID NO: 14 wherein the isolated polynucleotide may optionally be incorporated into a vector and wherein the kit may optionally contain one or more cell lines.

In certain embodiments the present invention provides a kit comprising an isolated polynucleotide has the amino acid sequence of SEQ ID NO: 18 wherein the isolated polynucleotide may optionally be incorporated into a vector and wherein the kit may optionally contain one or more cell lines.

In certain embodiments the present invention provides a kit comprising an isolated polynucleotide has the amino acid sequence of SEQ ID NO: 20 wherein the isolated polynucleotide may optionally be incorporated into a vector and wherein the kit may optionally contain one or more cell lines.

In certain embodiments the present invention provides a kit comprising an isolated polynucleotide has the amino acid sequence of SEQ ID NO: 24 wherein the isolated polynucleotide may optionally be incorporated into a vector and wherein the kit may optionally contain one or more cell lines.

In certain embodiments the present invention provides a kit comprising an isolated polynucleotide has the amino acid sequence of SEQ ID NO: 26 wherein the isolated polynucleotide may optionally be incorporated into a vector and wherein the kit may optionally contain one or more cell lines.

In certain embodiments the present invention provides a kit comprising one, two, three, four, five, six, seven, eight, or nine isolated polynucleotides has (have) the amino acid sequence selected from the group consisting of SEQ ID NOs:10, 12, 14, 16, 18, 20, 22, 24, and 26 wherein the isolated polynucleotide may optionally be incorporated into a vector and wherein the kit may optionally contain one or more cell lines.

In certain embodiments, the present invention provides a fusion protein of a variant polypeptide, wherein said variant polypeptide comprises at least 90% identity to SEQ ID NO:10. In certain embodiments, the variant polypeptide of the fusion protein comprises at least 95% identity to SEQ ID NO:10. In certain embodiments, the variant polypeptide of the fusion protein comprises SEQ ID NO:10. In certain embodiments, the variant polypeptide of the fusion protein has the amino acid sequence selected from the group consisting of SEQ ID NOs:12, 14, 16, 18, 20, 22, 24, and 26. In certain embodiments, the variant polypeptide of the fusion protein has the amino acid sequence of SEQ ID NO: 12. In certain embodiments, the variant polypeptide of the fusion protein has the amino acid sequence of SEQ ID NO: 14.

In certain embodiments, the present invention provides a fusion protein of an isolated polynucleotide encoding a polypeptide comprising at least 90% identity to SEQ ID NO:10. In certain embodiments the isolated polynucleotide of the fusion protein comprises at least 95% identity to SEQ ID NO:10. In certain embodiments the isolated polynucleotide of the fusion protein comprises SEQ ID NO:10. In certain embodiments the isolated polynucleotide of the fusion protein has the amino acid sequence selected from the group consisting of SEQ ID NOs:12, 14, 16, 18, 20, 22, 24, and 26. In certain embodiments the isolated polynucleotide of the fusion protein has the amino acid sequence of SEQ ID NO: 12. In certain embodiments the isolated polynucleotide of the fusion protein has the amino acid sequence of SEQ ID NO: 14.

In certain embodiments, the present invention provides a vector comprising a fusion protein of an isolated polynucleotide wherein the isolated polynucleotide comprises a polypeptide comprising at least 90% identity to SEQ ID NO:10. In certain embodiments the present invention provides a vector comprising a fusion protein of an isolated polynucleotide, wherein the isolated polypeptide comprises at least 95% identity to SEQ ID NO:10. In certain embodiments the present invention provides a vector comprising a fusion protein of an isolated polynucleotide, wherein the isolated polypeptide comprises SEQ ID NO:10. In certain embodiments the present invention provides a vector comprising a fusion protein of an isolated polynucleotide, wherein the isolated polypeptide comprises an amino acid sequence selected from the group consisting of SEQ ID NOs:12, 14, 16, 18, 20, 22, 24, and 26. In certain embodiments the present invention provides a vector comprising a fusion protein of an isolated polynucleotide, wherein the isolated polypeptide comprises SEQ ID NO: 12. In certain embodiments the present invention provides a vector comprising a fusion protein of an isolated polynucleotide, wherein the isolated polypeptide comprises SEQ ID NO: 14.

In certain embodiments, the present invention provides a host cell comprising a fusion protein of an isolated polynucleotide wherein the isolated polypeptide comprises at least 90% identity to SEQ ID NO:10. In certain embodiments the present invention provides a host cell comprising a fusion protein of an isolated polynucleotide wherein the isolated polypeptide comprises SEQ ID NO:10. In certain embodiments the present invention provides a host cell comprising a fusion protein of an isolated polynucleotide wherein the isolated polypeptide comprises SEQ ID NO:10. In certain embodiments the present invention provides a host cell comprising a fusion protein of an isolated polynucleotide wherein the isolated polypeptide comprises the amino acid sequence selected from the group consisting of SEQ ID NOs:12, 14, 16, 18, 20, 22, 24, and 26. In certain embodiments the present invention provides a host cell comprising a fusion protein of an isolated polynucleotide wherein the isolated polypeptide comprises SEQ ID NO: 12. In certain embodiments the present invention provides a host cell comprising a fusion protein of an isolated polynucleotide wherein the isolated polypeptide comprises SEQ ID NO: 14.

In certain embodiments, the present invention provides a kit comprising a fusion protein of an isolated polynucleotide wherein the isolated polypeptide comprises at least 90% identity to SEQ ID NO:10 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises at least 95% identity to SEQ ID NO:10 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO:10 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises an amino acid sequence selected from the group consisting of SEQ ID NOs:12, 14, 16, 18, 20, 22, 24, and 26 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO: 12 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO: 14 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO: 18 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO: 20 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO: 24 wherein the isolated polynucleotide may optionally be incorporated into a vector and wherein the kit may optionally contain one or more cell lines.

In certain embodiments the present invention provides a kit comprising a fusion protein of an isolated polynucleotide wherein the isolated polypeptide comprises SEQ ID NO: 26 wherein the isolated polynucleotide may optionally be incorporated into a vector and wherein the kit may optionally contain one or more cell lines.

In certain embodiments the present invention provides a kit comprising one, two, three, four, five, six, seven, eight, or nine fusion proteins of an isolated polynucleotide(s) wherein the isolated polynucleotide(s) has(have) the amino acid sequence selected from the group consisting of SEQ ID NOs:10, 12, 14, 16, 18, 20, 22, 24, and 26 wherein the isolated polynucleotide may optionally be incorporated into a vector and wherein the kit may optionally contain one or more cell lines.

In certain embodiments, the present invention provides a fusion protein of a variant polypeptide, wherein said variant polypeptide comprises at least 90% identity to SEQ ID NO:10 wherein the wherein fluorescence of the polypeptide is greater than 5-fold higher than IFP1.4.

In certain embodiments, the variant polypeptide of the fusion protein comprises at least 95% identity to SEQ ID NO:10 wherein the wherein fluorescence of the polypeptide is greater than 5-fold higher than IFP1.4.

In certain embodiments, the variant polypeptide of the fusion protein comprises SEQ ID NO:10.

In certain embodiments, the variant polypeptide of the fusion protein has the amino acid sequence selected from the group consisting of SEQ ID NOs:12, 14, 16, 18, 20, 22, 24, and 26 wherein the wherein fluorescence of the polypeptide is greater than 5-fold higher than IFP1.4.

In certain embodiments, the variant polypeptide of the fusion protein has the amino acid sequence of SEQ ID NO:

12 wherein the wherein fluorescence of the polypeptide is greater than 5-fold higher than IFP1.4.

In certain embodiments, the variant polypeptide of the fusion protein has the amino acid sequence of SEQ ID NO: 14 wherein the wherein fluorescence of the polypeptide is greater than 5-fold higher than IFP1.4.

In certain embodiments, the present invention provides a fusion protein of an isolated polynucleotide encoding a polypeptide comprising at least 90% identity to SEQ ID NO:10 wherein the wherein fluorescence of the polypeptide is greater than 5-fold higher than IFP1.4.

In certain embodiments the isolated polynucleotide of the fusion protein comprises at least 95% identity to SEQ ID NO:10 wherein the wherein fluorescence of the polypeptide is greater than 5-fold higher than IFP1.4.

In certain embodiments the isolated polynucleotide of the fusion protein comprises SEQ ID NO:10 wherein the wherein fluorescence of the polypeptide is greater than 5-fold higher than IFP1.4.

In certain embodiments the isolated polynucleotide of the fusion protein has the amino acid sequence selected from the group consisting of SEQ ID NOs:12, 14, 16, 18, 20, 22, 24, and 26 wherein the wherein fluorescence of the polypeptide is greater than 5-fold higher than IFP1.4.

In certain embodiments the isolated polynucleotide of the fusion protein has the amino acid sequence of SEQ ID NO: 12 wherein the wherein fluorescence of the polypeptide is greater than 5-fold higher than IFP1.4.

In certain embodiments the isolated polynucleotide of the fusion protein has the amino acid sequence of SEQ ID NO: 14 wherein the wherein fluorescence of the polypeptide is greater than 5-fold higher than IFP1.4.

In certain embodiments, the present invention provides a vector comprising a fusion protein of an isolated polynucleotide wherein the isolated polynucleotide comprises a polypeptide comprising at least 90% identity to SEQ ID NO:10 wherein the wherein fluorescence of the polypeptide is greater than 5-fold higher than IFP1.4.

In certain embodiments the present invention provides a vector comprising a fusion protein of an isolated polynucleotide, wherein the isolated polypeptide comprises at least 95% identity to SEQ ID NO:10 wherein the wherein fluorescence of the polypeptide is greater than 5-fold higher than IFP1.4.

In certain embodiments the present invention provides a vector comprising a fusion protein of an isolated polynucleotide, wherein the isolated polypeptide comprises SEQ ID NO:10 wherein the wherein fluorescence of the polypeptide is greater than 5-fold higher than IFP1.4.

In certain embodiments the present invention provides a vector comprising a fusion protein of an isolated polynucleotide, wherein the isolated polypeptide comprises an amino acid sequence selected from the group consisting of SEQ ID NOs:12, 14, 16, 18, 20, 22, 24, and 26 wherein the wherein fluorescence of the polypeptide is greater than 5-fold higher than IFP1.4.

In certain embodiments the present invention provides a vector comprising a fusion protein of an isolated polynucleotide, wherein the isolated polypeptide comprises SEQ ID NO: 12 wherein the wherein fluorescence of the polypeptide is greater than 5-fold higher than IFP1.4.

In certain embodiments the present invention provides a vector comprising a fusion protein of an isolated polynucleotide, wherein the isolated polypeptide comprises SEQ ID NO: 14 wherein the wherein fluorescence of the polypeptide is greater than 5-fold higher than IFP1.4.

In certain embodiments, the present invention provides a host cell comprising a fusion protein of an isolated polynucleotide wherein the isolated polypeptide comprises at least 90% identity to SEQ ID NO:10 wherein the wherein fluorescence of the polypeptide is greater than 5-fold higher than IFP1.4.

In certain embodiments the present invention provides a host cell comprising a fusion protein of an isolated polynucleotide wherein the isolated polypeptide comprises SEQ ID NO:10 wherein the wherein fluorescence of the polypeptide is greater than 5-fold higher than IFP1.4.

In certain embodiments the present invention provides a host cell comprising a fusion protein of an isolated polynucleotide wherein the isolated polypeptide comprises SEQ ID NO:10 wherein the wherein fluorescence of the polypeptide is greater than 5-fold higher than IFP1.4.

In certain embodiments the present invention provides a host cell comprising a fusion protein of an isolated polynucleotide wherein the isolated polypeptide comprises the amino acid sequence selected from the group consisting of SEQ ID NOs:12, 14, 16, 18, 20, 22, 24, and 26 wherein the wherein fluorescence of the polypeptide is greater than 5-fold higher than IFP1.4.

In certain embodiments the present invention provides a host cell comprising a fusion protein of an isolated polynucleotide wherein the isolated polypeptide comprises SEQ ID NO: 12 wherein the wherein fluorescence of the polypeptide is greater than 5-fold higher than IFP1.4.

In certain embodiments the present invention provides a host cell comprising a fusion protein of an isolated polynucleotide wherein the isolated polypeptide comprises SEQ ID NO: 14 wherein the wherein fluorescence of the polypeptide is greater than 5-fold higher than IFP1.4.

In certain embodiments, the present invention provides a kit comprising a fusion protein of an isolated polynucleotide wherein the isolated polypeptide comprises at least 90% identity to SEQ ID NO:10 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises at least 95% identity to SEQ ID NO:10 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO:10 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises an amino acid sequence selected from the group consisting of SEQ ID NOs:12, 14, 16, 18, 20, 22, 24, and 26 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO: 12 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO: 14 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO: 18 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO: 20 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO: 24 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising a fusion protein of an isolated polynucleotide wherein the isolated polypeptide comprises SEQ ID NO: 26 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments the present invention provides a kit comprising one, two, three, four, five, six, seven, eight, or nine fusion proteins of an isolated polynucleotide(s) wherein the isolated polynucleotide(s) has(have) the amino acid sequence selected from the group consisting of SEQ ID NOs:10, 12, 14, 16, 18, 20, 22, 24, and 26 wherein the isolated polynucleotide may optionally be incorporated into a vector and wherein the kit may optionally contain one or more cell lines wherein the wherein fluorescence of the polypeptide is greater than 5-fold higher than IFP1.4.

In certain embodiments, the present invention provides a fusion protein of a variant polypeptide, wherein said variant polypeptide comprises at least 90% identity to SEQ ID NO:10 wherein the wherein fluorescence of the polypeptide is greater than 10-fold higher than IFP1.4.

In certain embodiments, the variant polypeptide of the fusion protein comprises at least 95% identity to SEQ ID NO:10 wherein the wherein fluorescence of the polypeptide is greater than 10-fold higher than IFP1.4.

In certain embodiments, the variant polypeptide of the fusion protein comprises SEQ ID NO:10.

In certain embodiments, the variant polypeptide of the fusion protein has the amino acid sequence selected from the group consisting of SEQ ID NOs:12, 14, 16, 18, 20, 22, 24, and 26 wherein the wherein fluorescence of the polypeptide is greater than 10-fold higher than IFP1.4.

In certain embodiments, the variant polypeptide of the fusion protein has the amino acid sequence of SEQ ID NO: 12 wherein the wherein fluorescence of the polypeptide is greater than 10-fold higher than IFP1.4.

In certain embodiments, the variant polypeptide of the fusion protein has the amino acid sequence of SEQ ID NO: 14 wherein the wherein fluorescence of the polypeptide is greater than 10-fold higher than IFP1.4.

In certain embodiments, the present invention provides a fusion protein of an isolated polynucleotide encoding a polypeptide comprising at least 90% identity to SEQ ID NO:10 wherein the wherein fluorescence of the polypeptide is greater than 10-fold higher than IFP1.4.

In certain embodiments the isolated polynucleotide of the fusion protein comprises at least 95% identity to SEQ ID NO:10 wherein the wherein fluorescence of the polypeptide is greater than 10-fold higher than IFP1.4.

In certain embodiments the isolated polynucleotide of the fusion protein comprises SEQ ID NO:10 wherein the wherein fluorescence of the polypeptide is greater than 10-fold higher than IFP1.4.

In certain embodiments the isolated polynucleotide of the fusion protein has the amino acid sequence selected from the group consisting of SEQ ID NOs:12, 14, 16, 18, 20, 22, 24, and 26 wherein the wherein fluorescence of the polypeptide is greater than 10-fold higher than IFP1.4.

In certain embodiments the isolated polynucleotide of the fusion protein has the amino acid sequence of SEQ ID NO: 12 wherein the wherein fluorescence of the polypeptide is greater than 10-fold higher than IFP1.4.

In certain embodiments the isolated polynucleotide of the fusion protein has the amino acid sequence of SEQ ID NO: 14 wherein the wherein fluorescence of the polypeptide is greater than 10-fold higher than IFP1.4.

In certain embodiments, the present invention provides a vector comprising a fusion protein of an isolated polynucleotide wherein the isolated polynucleotide comprises a polypeptide comprising at least 90% identity to SEQ ID NO:10 wherein the wherein fluorescence of the polypeptide is greater than 10-fold higher than IFP1.4.

In certain embodiments the present invention provides a vector comprising a fusion protein of an isolated polynucleotide, wherein the isolated polypeptide comprises at least 95% identity to SEQ ID NO:10 wherein the wherein fluorescence of the polypeptide is greater than 10-fold higher than IFP1.4.

In certain embodiments the present invention provides a vector comprising a fusion protein of an isolated polynucleotide, wherein the isolated polypeptide comprises SEQ ID NO:10 wherein the wherein fluorescence of the polypeptide is greater than 10-fold higher than IFP1.4.

In certain embodiments the present invention provides a vector comprising a fusion protein of an isolated polynucleotide, wherein the isolated polypeptide comprises an amino acid sequence selected from the group consisting of SEQ ID NOs:12, 14, 16, 18, 20, 22, 24, and 26 wherein the wherein fluorescence of the polypeptide is greater than 10-fold higher than IFP1.4.

In certain embodiments the present invention provides a vector comprising a fusion protein of an isolated polynucleotide, wherein the isolated polypeptide comprises SEQ ID NO: 12 wherein the wherein fluorescence of the polypeptide is greater than 10-fold higher than IFP1.4.

In certain embodiments the present invention provides a vector comprising a fusion protein of an isolated polynucleotide, wherein the isolated polypeptide comprises SEQ ID NO: 14 wherein the wherein fluorescence of the polypeptide is greater than 10-fold higher than IFP1.4.

In certain embodiments, the present invention provides a host cell comprising a fusion protein of an isolated polynucleotide wherein the isolated polypeptide comprises at least 90% identity to SEQ ID NO:10 wherein the wherein fluorescence of the polypeptide is greater than 10-fold higher than IFP1.4.

In certain embodiments the present invention provides a host cell comprising a fusion protein of an isolated polynucleotide wherein the isolated polypeptide comprises SEQ ID NO:10 wherein the wherein fluorescence of the polypeptide is greater than 10-fold higher than IFP1.4.

In certain embodiments the present invention provides a host cell comprising a fusion protein of an isolated polynucleotide wherein the isolated polypeptide comprises SEQ ID NO:10 wherein the wherein fluorescence of the polypeptide is greater than 10-fold higher than IFP1.4.

In certain embodiments the present invention provides a host cell comprising a fusion protein of an isolated polynucleotide wherein the isolated polypeptide comprises the amino acid sequence selected from the group consisting of SEQ ID NOs:12, 14, 16, 18, 20, 22, 24, and 26 wherein the wherein fluorescence of the polypeptide is greater than 10-fold higher than IFP1.4.

In certain embodiments the present invention provides a host cell comprising a fusion protein of an isolated polynucleotide wherein the isolated polypeptide comprises SEQ ID NO: 12 wherein the wherein fluorescence of the polypeptide is greater than 10-fold higher than IFP1.4.

In certain embodiments the present invention provides a host cell comprising a fusion protein of an isolated polynucleotide wherein the isolated polypeptide comprises SEQ ID NO: 14 wherein the wherein fluorescence of the polypeptide is greater than 10-fold higher than IFP1.4.

In certain embodiments, the present invention provides a kit comprising a fusion protein of an isolated polynucleotide wherein the isolated polypeptide comprises at least 90% identity to SEQ ID NO:10 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises at least 95% identity to SEQ ID NO:10 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO:10 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises an amino acid sequence selected from the group consisting of SEQ ID NOs:12, 14, 16, 18, 20, 22, 24, and 26 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO: 12 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO: 14 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO: 18 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO: 20 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO: 24 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising a fusion protein of an isolated polynucleotide wherein the isolated polypeptide comprises SEQ ID NO: 26 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments the present invention provides a kit comprising one, two, three, four, five, six, seven, eight, or nine fusion proteins of an isolated polynucleotide(s) wherein the isolated polynucleotide(s) has(have) the amino acid sequence selected from the group consisting of SEQ ID NOs:10, 12, 14, 16, 18, 20, 22, 24, and 26 wherein the isolated polynucleotide may optionally be incorporated into a vector and wherein the kit may optionally contain one or more cell lines wherein the wherein fluorescence of the polypeptide is greater than 10-fold higher than IFP1.4.

In certain embodiments, the present invention provides a method of in vivo optical imaging, the method comprising the step of: expressing in a cell a polynucleotide encoding a first protein, the first protein comprising a protein encoded by a polynucleotide comprising at least 90% to SEQ ID NO:10. In certain embodiments, the present invention provides a method of in vivo optical imaging, the method comprising the step of: expressing in a cell a polynucleotide encoding a first protein, the first protein comprising a protein encoded by a polynucleotide comprising at least 95% to SEQ ID NO:10. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:10.

In certain embodiments, the a method of in vivo optical imaging comprises a polynucleotide comprising an amino acid sequence consisting of SEQ ID NO:12. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:12; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:14. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:14; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:16. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:16; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:18. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:18; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:20. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:20; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:22. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:22; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:24. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:24; wherein the cell is a prokaryotic or eukaryotic cell, wherein some embodiments the cell is a mammalian cell and wherein some embodiments the cell is a mammalian cell in a whole, living organism.

In certain embodiments, the a method of in vivo optical imaging comprises a polynucleotide comprising an amino acid sequence consisting of SEQ ID NO:26. In certain embodiments, the present invention provides a method of in vivo optical imaging, the method comprising the step of: expressing in a cell a polynucleotide encoding a first protein, the first protein comprising a protein encoded by a polynucleotide comprising SEQ ID NO:26; wherein the cell is a prokaryotic or eukaryotic cell, wherein some embodiments the cell is a mammalian cell and wherein some embodiments the cell is a mammalian cell in a whole, living organism.

In certain embodiments, the present invention provides a method of detecting a cancer cell in vivo, the method comprising administering to a patient with cancer a fusion protein of a variant polypeptide of a parent polypeptide, wherein said variant polypeptide comprises at least 90% identity to SEQ ID NO:2, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises at least 95% identity to SEQ ID NO:2, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises SEQ ID NO:2, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises at least one amino acid substitution at a position selected from the group consisting of position 2, 8, 14, 74, 107, 128, 146, 156, 168, 175, 178, 185, 199, 210, 256, 258, 292, 310, and 320, wherein the numbering of the amino acid positions correspond to that in native BrBphP from *Bradyrhizobium* sp. ORS278, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises at least one amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises one, two, three, four, five, six, seven, eight, nine, ten, eleven, twelve, thirteen, fourteen, fifteen, sixteen, seventeen, eighteen, or nineteen amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises the amino acid substitutions 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide of a parent polypeptide, wherein said variant polypeptide comprises at least 90% identity to SEQ ID NO:2, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises at least 95% identity to SEQ ID NO:2, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises SEQ ID NO:2, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises at least one amino acid substitution at a position selected from the group consisting of position 2, 8, 14, 74, 107, 128, 146, 156, 168, 175, 178, 185, 199, 210, 256, 258, 292, 310, and 320, wherein the numbering of the amino acid positions correspond to that in native BrBphP from *Bradyrhizobium* sp. ORS278, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises at least one amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises one, two, three, four, five, six, seven, eight, nine, ten, eleven, twelve, thirteen, fourteen, fifteen, sixteen, seventeen, eighteen, or nineteen amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises the amino acid substitutions 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide of a parent polypeptide, wherein said variant polypeptide comprises at least 90% identity to SEQ ID NO:2, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises at least 95% identity to SEQ ID NO:2, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises SEQ ID NO:2, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises at least one amino acid substitution at a position selected from the group consisting of position 2, 8, 14, 74, 107, 128, 146, 156, 168, 175, 178, 185, 199, 210, 256, 258, 292, 310, and 320, wherein the numbering of the amino acid positions correspond to that in native BrBphP from *Bradyrhizobium* sp. ORS278, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises at least one amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises one, two, three, four, five, six, seven, eight, nine, ten, eleven, twelve, thirteen, fourteen, fifteen, sixteen, seventeen, eighteen, or nineteen amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises the amino acid substitutions 2S, 8S, 14F, 74P, 107I, 128I, 146M, 156I, 168V, 175N, 178I, 185A, 199T, 210H, 256M, 258D, 292H, 310T, and 320K, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide of a parent polypeptide, wherein said variant polypeptide comprises at least 90% identity to SEQ ID NO:10, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which comprises at least 95% identity to SEQ ID NO:10, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence selected from the group consisting of SEQ ID NOs:12, 14, 16, 18, 20, 22, 24, and 26, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:12, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:14, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:16, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:18, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:20, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:22, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:24, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide which has the amino acid sequence of SEQ ID NO:26, wherein the fusion protein binds to a cancer cell, and detecting the fluorescence of the variant polypeptide.

In certain embodiments, the present invention provides a method of detecting a cancer cell in vivo, the method comprising administering to a patient with cancer a fusion protein of a variant polypeptide of a parent polypeptide, wherein said variant polypeptide comprises at least 90% identity to SEQ ID NO:10, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which comprises at least 95% identity to SEQ ID NO:10, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence selected from the group consisting of SEQ ID NOs:12, 14, 16, 18, 20, 22, 24, and 26, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:12, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:14, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:16, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:18, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:20, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:22, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:24, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:26, wherein the fusion protein binds to a cancer cell, and detecting the fluorescence of the variant polypeptide, wherein fluorescence of the polypeptide is greater than 5-fold higher than IFP1.4.

In certain embodiments, the present invention provides a method of detecting a cancer cell in vivo, the method comprising administering to a patient with cancer a fusion protein of a variant polypeptide of a parent polypeptide, wherein said variant polypeptide comprises at least 90% identity to SEQ ID NO:10, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which comprises at least 95% identity to SEQ ID NO:10, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence selected from the group consisting of SEQ ID NOs:12, 14, 16, 18, 20, 22, 24, and 26, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:12, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:14, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:16, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:18, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:20, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:22, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:24, wherein the fusion protein binds to a cancer cell, and detecting the fluorescence of the variant polypeptide, wherein fluorescence of the polypeptide is greater than 10-fold higher than IFP1.4.

In certain embodiments, the present invention provides a method of detecting a cancer cell in vivo, the method comprising administering to a patient with cancer a fusion protein of a variant polypeptide which has the amino acid sequence of SEQ ID NO:26, wherein the fusion protein binds to a cancer cell, and detecting the fluorescence of the variant polypeptide, wherein fluorescence of the polypeptide is greater than 10-fold higher than IFP1.4.

In certain embodiments, the fusion protein is an antibody-variant polypeptide fusion protein.

In certain embodiments, the fusion protein is a ligand-variant polypeptide fusion protein. In certain embodiments, the ligand binds EGFR.

BRIEF DESCRIPTION OF THE DRAWINGS

FIG. 1 illustrates the DNA and protein sequence of mIFP. Further shown are the BrCBD (i.e., the truncated mutant of BrBphP) to mIFP amino acid substitutions. mIFP was engineered from a bacterial phytochrome, BrBphP, from *Bradyrhizobium* sp. ORS278. BrBphP contains 724 amino acids. As described herein, a truncated mutant of BrBphP, named BrCBD, was created which contains 320 amino acids, starting from amino acid 1 (.e., from N-terminus of BrBphP). Then 19 mutations were introduced into BrCBD through directed evolution.

FIG. 2 illustrates an alignment of the amino acid sequence of mIFP and BrCDB. Mutated residues are highlighted.

DETAILED DESCRIPTION OF THE INVENTION

Introduction

Figure 3:
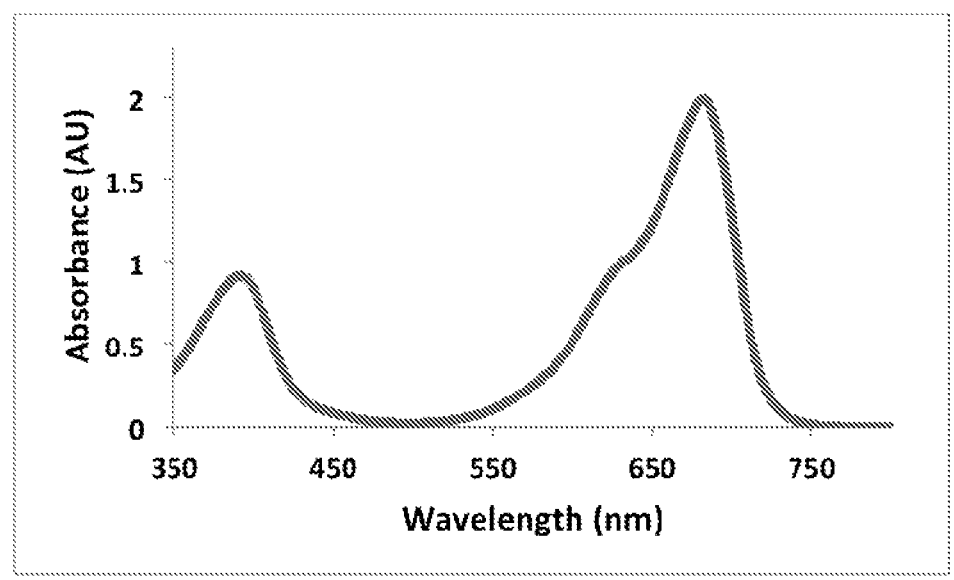
FIG. 3 illustrates the photophysical properties of mIFP. The absorbance spectrum shows that the maximal absorbance wavelength is 683 nm.

GFP and its red homologs are powerful tools for cell and molecular biology (Day, R. N. & Davidson, M. W. The fluorescent protein palette: tools for cellular imaging. *Chem Soc Rev* 38, 2887-2921 (2009); Tsien, R. Y. Constructing and exploiting the fluorescent protein paintbox (Nobel Lecture). *Angew Chem Int Ed Engl* 48, 5612-5626 (2009)). Through protein engineering, these fluorescent proteins (FPs) now cover UV-visible spectrum every ~30 nm from 400 to 600 nm (excitation maxima) (Kremers, G. J., Gilbert, S. G., Cranfill, P. J., Davidson, M. W. & Piston, D. W. Fluorescent proteins at a glance. *Journal of Cell Science* 124, 2676-2676 (2011)). They have been widely used in multicolor protein labeling in living cells, which enables study of spatiotemporal dynamics of multiple proteins and protein-protein interactions (Sakaue-Sawano, A. et al. Visualizing Spatiotemporal Dynamics of Multicellular Cell-Cycle Progression. *Cell* 132, 487-498 (2008)). They have also been used in developing other technologies such as genetically encoded Forster (or fluorescence) resonance energy transfer (FRET) for reporting activities of an enzyme such as kinase (Zhang, J., Hupfeld, C. J., Taylor, S. S., Olefsky, J. M. & Tsien, R. Y. Insulin disrupts beta-adrenergic signalling to protein kinase A in adipocytes. *Nature* 437, 569-573 (2005); Wang, Y. et al. Visualizing the mechanical activation of Src. *Nature* 434, 1040-1045 (2005)), and monitoring small signaling molecules such as calcium and cAMP (Miyawaki, A. et al. Fluorescent indicators for Ca2+ based on green fluorescent proteins and calmodulin. *Nature* 388, 882-887 (1997); Zaccolo, M. Discrete Microdomains with High Concentration of cAMP in Stimulated Rat Neonatal Cardiac Myocytes. *Science* 295, 1711-1715 (2002)).

Recently, this FP palette has been extended into the near-infrared region by the introduction of bacterial phytochrome-derived IFPs of which the scaffold is different from the β-can fold of GFP (Shu, X. et al. Mammalian expression of infrared fluorescent proteins engineered from a bacterial phytochrome. *Science* 324, 804-807 (2009); Filonov, G. S. et al. Bright and stable near-infrared fluorescent protein for in vivo imaging. *Nat Biotechnol* 29, 757-761 (2011)). Bacterial phytochromes belong to the phytochrome (Phy) red/far-red photoreceptor superfamily (Giraud, E. & Verméglio, A. Bacteriophytochromes in anoxygenic photosynthetic bacteria. *Photosyn Res* 97, 141-153 (2008)). In addition to BphPs, the Phy superfamily also includes plant phytochromes (Phys), cyanobacterial phytochromes (Cphs) and fungal phytochromes (Fphs) (Karniol, B., Wagner, J. R., Walker, J. M. & Vierstra, R. D. Phylogenetic analysis of the phytochrome superfamily reveals distinct microbial subfamilies of photoreceptors. *Biochem J* 392, 103 (2005)).

The Phy superfamily utilizes a covalently bound tetrapyrrole bilin to sense red and far-red, which allows the organism to adapt to changes of light environment. BphPs use a linear tetrapyrrole bilin, biliverdin (BV), which is a catabolic metabolite of heme by heme oxygenase. BphPs are composed of an N-terminal PAS domain, followed by GAF domain and PHY domain, and a signal transduction domain at C-terminus that is often a histidine kinase. BphPs contain intrinsic lyase activity and therefore they autocatalytically incorporate the bilin chromophore. BV binds to GAF domain non-covalently and forms a thioether bond between its A-ring vinyl group and a conserved cysteine at N-terminus (Wagner, J. R., Brunzelle, J. S., Forest, K. T. & Vierstra, R. D. A light-sensing knot revealed by the structure of the chromophore-binding domain of phytochrome. *Nature* 438, 325-331 (2005)).

Upon light excitation the D-ring of BV rotates, resulting in a conformational change of the protein and leads to activation of histidine kinase (Yang, X., Ren, Z., Kuk, J. & Moffat, K. Temperature-scan cryocrystallography reveals reaction intermediates in bacteriophytochrome. *Nature* 479, 428-432 (2011)). This kinase activation results in changes of gene expression, which allows optimal development of bacteria according to the light environment (Giraud, E. & Verméglio, A. Bacteriophytochromes in anoxygenic photosynthetic bacteria. *Photosyn Res* 97, 141-153 (2008)). This biological function suggests that BphPs are highly efficient at non-radiative decay of its excited state, and therefore the radiative decay efficiency is negligible. In other words, BphPs are probably optimized through evolution to be non-fluorescent.

BphPs, on the other hand, absorb at 700 nm, which is 100 nm redshifted compared to far-red FPs with the GFP fold. Because of this advantage and that BV is an endogenous molecule in mammalian cells, a DrBphP (a BphP from *Deinoccocus Radiodurans*) was engineered into IFP1.4 by structure-guided mutagenesis (Shu, X. et al. Mammalian expression of infrared fluorescent proteins engineered from a bacterial phytochrome. *Science* 324, 804-807 (2009)). Specifically, DrBphP was truncated to contain only the PAS and GAF domains (i.e., the two domains which, when expressed alone, are sufficient for BV binding). The D-ring binding cavity of the GAF domain was also engineered to rigidify the D-ring. Through this directed evolution, a fluorescent mutant IFP1.4 was obtained which can be expressed and fluoresces in mammalian cells. Subsequently, RpBphP2 (a BphP from *Rhodopseudomonas palustris*) was engineered into a fluorescent mutant iRFP using similar strategies (Filonov, G. S. et al. Bright and stable near-infrared fluorescent protein for in vivo imaging. *Nat Biotechnol* 29, 757-761 (2011)).

BphP-derived IFPs can provide an orthogonal color to GFP and its red homologs in protein labeling. As a protein fusion tag, FP has to be monomeric so that it will not perturb the stoichiometry of the protein of interest. However, most Phys including BphPs function as multimeric complexes through oligomeric interaction at the N-terminal photosensory core domain (PAS-GAF-PHY) or at the C-terminal module (Giraud, E. & Verméglio, A. Bacteriophytochromes in anoxygenic photosynthetic bacteria. *Photosyn Res* 97, 141-153 (2008)). Both IFP1.4 and iRFP were derived from dimeric BphPs.

The invention described herein discloses infrared fluorescent proteins and protein variants. Specifically, IFPs that are mutants of a phytochrome from the bacterium *Bradyrhizobium* sp. ORS278 are disclosed herein. The variants are monomeric, allowing them to be used as a protein tag without disrupting the function of the tagged protein of interest. Because infrared light penetrates through tissue more efficiently, the variants are particularly suited for fluorescent imaging of deep tissues in whole animals, including mice and humans. Thus, monomeric infrared fluorescent proteins can be used to study drug effects on tissues or to track tagged cancer cells.

One variant described by the present invention is mIFP (monomeric Infrared Fluorescent Protein), which was engineered from the bacterial phytochrome BrBphP, from the bacterium *Bradyrhizobium* sp. ORS278 (Giraud et al., *Nature* 417:202-205 (2002)). mIFP exhibits an approximate ten-fold increase in brightness compared to another infrared fluorescent protein known as IFP1.4 (Shu et al., *Science* 324:804-807 (2009)).

As described herein, this invention describes the development of a robust protein tag in the infrared spectrum. First, a naturally monomeric BphP was identified from protein sequence database using structural and sequence analysis. Second, the naturally monomeric BphP was engineered into a monomeric IFP (mIFP). Unlike previous IFPs, this mIFP can readily be used as a protein tag. Rationally designed blueshifted mutants, iBlueberry, are also described herein. iBlueberry bridges the spectral gap between GFP-like far-red FPs and mIFP. iBlueberry and mIFP expand the palette of FPs in protein labeling by adding two orthogonal colors.

Certain aspects of this invention include the use of the novel IFPs described herein as a protein fusion tag. Specifically, because mIFP is monomeric, it can be used as a protein tag with no or little perturbation to the protein of interest. A second aspect of this invention includes the use of the novel IFPs described herein for whole animal imaging. Because infrared light penetrates through tissue more efficiently than visible light, mIFP is best suited for fluorescence imaging of deep tissues in whole animals including mice. Furthermore, a third aspect of this invention includes the use of the IFPs disclosed herein for imaging via energy transfer. Specifically, technologies such as fluorescence resonance energy transfer (FRET) can be developed based on iBlueberry and mIFP. Such FRET sensors can be used orthogonally with GFP-based FRET sensors since they are spectrally separated.

In contrast to the known fluorescent proteins in the art, the IFPs described herein have distinct advantages. For example, when expressed in cells, mIFP is ~10 times brighter compared to IFP1.4, another infrared fluorescent protein. Furthermore, mIFP is monomeric whereas iRFP is dimeric. iRFP forms strong dimer which will force two copies of fused protein of interest to come together. Therefore, iRFP is likely to perturb protein interaction and is not suitable as a protein fusion tag.

Definitions

Unless specifically indicated otherwise, all technical and scientific terms used herein have the same meaning as commonly understood by those of ordinary skill in the art to which this invention belongs. In addition, method or materials that are substantially equivalent to a method or material described herein can be used in the practice of the present invention. For purposes of the present invention, the following terms are defined.

"A" or "the" as used herein not only includes aspects with one member, but also includes aspects with more than one member. For example, an embodiment including "an IFP" should be understood to present certain aspects with two or more IFPs.

"Or" as used herein should in general be construed non-exclusively. For example, an embodiment of "a variant phytochrome comprising the mutations E158V, A185S, or I203N" would typically present aspects with any one, two, or all three of the mutations.

The term "phytochrome" refers to a class of plant- and bacteria-derived proteins. Naturally occurring, non-mutant phytochromes generally absorb in the red portion of the visible spectrum. "Bacteriophytochrome" refers to a phytochrome derived from bacteria.

The term "isolated" as used herein with respect to nucleic acids, such as DNA or RNA, refers to molecules separated from other DNAs, or RNAs, respectively that are present in the natural source of the macromolecule. Isolated is meant to include nucleic acid fragments which are not naturally occurring as fragments and would not be found in the natural state. The term isolated as used herein also refers to a nucleic acid or peptide that is substantially free of cellular material, viral material, or culture medium when produced by recombinant DNA techniques, or chemical precursors, or other chemicals when chemically synthesized.

More broadly, the term "isolated" or "purified" refers to a material that is substantially or essentially free from other components that normally accompany the material in its native state in nature. Purity or homogeneity generally are determined using analytical chemistry techniques such as polyacrylamide gel electrophoresis, high-performance liquid chromatography (HPLC), and the like. A polynucleotide or a polypeptide is considered to be isolated when it is the predominant species present in a preparation. Generally, an isolated protein or nucleic acid molecule represents greater than 50% of the macromolecular species present in a preparation, usually represents greater than 80% or 90% of all macromolecular species present, often represents greater than 95%, of the macromolecular species, and, in particular, may be a polypeptide or polynucleotide that purified to essential homogeneity such that it is the only species detected when it is examined using conventional methods for determining the purity of such a molecule.

The term "naturally occurring" is used to refer to a protein, nucleic acid molecule, cell, or other material that exists in the natural world, for example, a polypeptide or polynucleotide sequence that is present in an organism, including in a virus. In general, at least one instance of a naturally occurring material existed in the world prior to its creation, duplication, or identification by a human. A naturally occurring material can be in its form as it exists in the natural world, or can be modified by the hand of man such that, for example, it is in an isolated form.

The term "nucleic acid" or "polynucleotide" refers to deoxyribonucleotides or ribonucleotides and polymers thereof in either single- or double-stranded form, and complements thereof. The term refers to all forms of nucleic acids (e.g., gene, pre-mRNA, mRNA) and their polymorphic variants, alleles, mutants, and interspecies homologs. The term nucleic acid is used interchangeably with gene, cDNA, mRNA, oligonucleotide, and polynucleotide. The term encompasses nucleic acids that are naturally occurring or recombinant. Nucleic acids can (1) code for an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence.

Relating specifically to the non-naturally occurring IFPs described herein, the term "polynucleotide" includes, but is not limited, to cDNA and RNA.

A particular nucleic acid sequence also implicitly encompasses "splice variants" and nucleic acid sequences encoding truncated forms of a protein. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N terminal end or the C-terminal end. Truncated versions of nucleic acid or polypeptide sequences can be naturally occurring or recombinantly created.

Nucleic acids can contain known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein variant of the invention linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced there from, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

An expression control sequence refers to a nucleotide sequence that regulates the transcription or translation of a polynucleotide or the localization of a polypeptide to which it is operatively linked Expression control sequences are "operatively linked" when the expression control sequence regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cistemae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the presequence of subunit IV of cytochrome c oxidase (see also Hancock et al., *EMBO J.* 10:4033-4039, 1991; Buss et al., *Mol. Cell. Biol.* 8:3960-3963, 1988; and U.S. Pat. No. 5,776,689; each of which is incorporated herein by reference).

The term "operatively linked" or "operably linked" or "operatively joined" or the like, when used to describe chimeric (i.e., fusion) proteins, refer to polypeptide sequences that are placed in a physical and functional relationship to each other. In a most preferred embodiment, the functions of the polypeptide components of the chimeric protein are unchanged compared to the functional activities of the parts in isolation. For example, a fluorescent protein of the present invention can be fused to a polypeptide of interest. In this case, it is preferable that the fusion molecule retains its fluorescence, and the polypeptide of interest retains its original biological activity. In some embodiments of the present invention, the activities of either the fluorescent protein or the protein of interest can be reduced relative to their activities in isolation. Such fusions can also find use with the present invention. As used herein, the fusion proteins of the invention can be in a monomeric state, or in a multimeric state (e.g., dimeric).

As used herein, the term "brightness," with reference to a fluorescent protein, is measured as the product of the extinction coefficient (EC) at a given wavelength and the fluorescence quantum yield (QY).

As used herein, the term "IR" or "infrared" includes wavelengths in the infrared and far red spectrum. One of skill in the art is able to measure the emission wavelength of each of the fluorescent molecules described herein to determine whether an individual molecule should be classified as infrared or far red.

The term "probe" refers to a substance that specifically binds to another substance (a "target"). Probes include, for example, antibodies, polynucleotides, receptors and their ligands, and generally can be labeled so as to provide a means to identify or isolate a molecule to which the probe has specifically bound.

The term "label" refers to a composition that is detectable with or without instrumentation, for example, by visual inspection, spectroscopy, or a photochemical, biochemical, immunochemical, or chemical reaction. Useful labels include, for example, phosphorus-32, a fluorescent dye, a fluorescent protein, an electron-dense reagent, an enzyme such as is commonly used in an ELISA, or a small molecule (such as biotin, digoxigenin, or other haptens or peptides) for which an antiserum or antibody, which can be a monoclonal antibody, is available. It will be recognized that a fluorescent protein variant of the invention, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and the isolation of the expressed protein, respectively. A label useful for purposes of the present invention generally generates a measurable signal such as a radioactive signal, fluorescent light, enzyme activity, and the like, either of which can be used, for example, to quantitate the amount of the fluorescent protein variant in a sample.

The term "polypeptide" or "protein" refers to a polymer of two or more amino acid residues. The terms apply to amino acid polymers in which one or more amino acid residue is an artificial, chemical analogue of a corresponding naturally occurring amino acid, as well as to polymers of naturally occurring amino acids. The term "recombinant protein" refers to a protein that is produced by expression of a nucleotide sequence encoding the amino acid sequence of the protein from a recombinant DNA molecule.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized. Antibodies exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

The term "immunoassay" refers to an assay that utilizes an antibody to specifically bind an analyte. An immunoassay is characterized by the use of specific binding properties of a particular antibody to isolate, to target, or to quantify the analyte.

The term "identical" or "identity" or "percent identity," or "sequence identity" in the context of two or more nucleic acids or polypeptide sequences that correspond to each other refer to two or more sequences or subsequences that are the same or have a specified percentage of amino acid residues or nucleotides that are the same (e.g., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical" and are embraced by the term "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists for a specified entire sequence or a specified portion thereof or over a region of the sequence that is at least about 25 amino acids or nucleotides in length, or more preferably over a region that is 50-100 amino acids or nucleotides in length. A corresponding region is any region within the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted (e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein.

Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids are well known in the art, including the following six groups, each of which contains amino acids that are considered conservative substitutes for each another:

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K)
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 90% sequence identity with each other, or with a reference sequence over a given comparison window. Thus, substantially similar sequences include those having, for example, at least 90% sequence identity, at least 95% sequence identity, at least 97% sequence identity, or at least 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C.

lower than the thermal melting point ($T_m$) for the specific sequence at a defined ionic strength and pH. The $T_m$ is the temperature, under defined ionic strength and pH, at which 50% of the target sequence hybridizes to a perfectly matched probe.

Fluorescent molecules are useful in fluorescence resonance energy transfer (FRET), which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize Ro, which represents the distance at which energy transfer efficiency is 50%. However, the excitation spectra of the donor and acceptor should overlap as little as possible so that a wavelength region can be found at which the donor can be excited efficiently without directly exciting the acceptor: Fluorescence arising from direct excitation of the acceptor can be difficult to distinguish from fluorescence arising from FRET. Similarly, the emission spectra of the donor and acceptor should overlap as little as possible so that the two emissions can be clearly distinguished. High-fluorescence quantum yield of the acceptor moiety is desirable if the emission from the acceptor is to be measured either as the sole readout or as part of an emission ratio. One factor to be considered in choosing the donor and acceptor pair is the efficiency of FRET between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between wild-type *Bradyrhizobium* fluorescent proteins and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing", respectively) are particularly advantageous because the ratioing process provides an internal reference and cancels out variations in the absolute brightness of the excitation source, the sensitivity of the detector, and light scattering or quenching by the sample.

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for preparing a composition of the invention or for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of the *Bradyrhizobium* sp. phytochrome can be derived from the naturally occurring phytochrome by engineering mutations such as amino acid substitutions into the reference protein.

The term "infrared fluorescent protein," or "IFP" is used in the broadest sense. Although it specifically covers the *Bradyrhizobium* sp. ORS278 phytochrome BrBphP, it also refers to fluorescent proteins from any other species and variant proteins thereof as long as they retain the ability to fluoresce infrared light.

As used herein, reference to a "related fluorescent protein" refers to a fluorescent protein that has a substantially identical amino acid sequence when compared to a reference fluorescent protein. In general, a related fluorescent protein, when compared to the reference fluorescent protein sequence, has a contiguous sequence of at least about 150 amino acids that shares at least about 80%, or at least about 85%, 86%, 87%, 88%, 89%, 90%, 91%, 92%, 93%, 94%, 95%, 96%, 97%, 98%, 99%, or more sequence identity with the reference fluorescent protein, and particularly has a contiguous sequence of at least about 200 amino acids that shares at least about 95% sequence identity with the reference fluorescent protein. In yet other embodiments, the related fluorescent protein may be compared over a region of about 50, or about 75, 100, 125, 150, 200, 250, 300, 350, or the full-length of the protein.

As used herein, the term "IFP-conjugate" and "fusion protein" refer to an IFP protein that is conjugated to a moiety. In certain embodiments the moiety targets a specific protein. For example, an IFP-conjugate can be an IFP-antibody conjugate. In a second non-limiting example, the IFP-conjugate can be an IFP-protein conjugate (e.g., a protein that localizes in particular organelles of a cell or an protein that binds to receptors of cells). For example, the IFP can be genetically engineered to express on a cytosolic protein to target and label the cytosol of transfected cell. An IFP-protein conjugate may also be an IFP that is conjugated to a ligand that binds certain receptors (e.g., EGFR) that are differentially expressed on cancer cells. The IFP-conjugate can be a genetically encoded conjugate such as a single polynucleotide that encodes a chimeric protein (e.g., an actin-IFP or ligand-IFP chimera). Alternatively, the IFP-conjugate can be formed from one or more covalent bonds. For example, an IFP can be linked to an antibody by one or more disulfide bonds.

The term "mutant" or "variant" also is used herein in reference to a fluorescent protein that contains a mutation with respect to a corresponding wild type fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

The term "substitution" refers to includes the replacement of one or more amino acid residues either by other naturally occurring amino acids, (conservative and non-conservative substitutions), by non-naturally occurring amino acids (conservative and non-conservative substitutions), or with organic moieties which serve either as true peptidoniimetics (e.g., having the same steric and electrochemical properties as the replaced amino acid), or merely serve as spacers in lieu of an amino acid, so as to keep the spatial relations between the amino acid spanning this replaced amino acid.

Infrared Fluorescent Proteins

The mIFPs of the present invention replace or supplement existing GFP and RFP variants in many applications because the near-infrared wavelengths of fluorescence with biliverdin as cofactor penetrate thick and pigmented tissue much better, have less background due to cellular autofluorescence, are more easily excited by cheap and versatile semiconductor light sources such as laser diodes, and can be detected with no interference from most standard fluorophores. The ability to load the same protein with protoporphyrin IX adds the possibility of correlated electron-microscopic visualization (e.g., usage as a contrast agent), detection and measurement of long-range protein-protein interactions, and controlled photoablation of the host cell or protein. A great many different phytochromes exist in bacteria and plants, so there is abundant raw material from which to evolve other IFPs.

mIFPs can be imaged over spatial scales from subcellular resolution up to strongly pigmented organs within intact whole mammals, whereas luciferase-based bioluminescence is useful mainly for whole-body imaging (C. H. Contag, M. H. Bachmann, *Annu. Rev. Biomed. Eng.* 4, 235 (2002)). The wavelengths of mIFPs are particularly well-suited to optical tomographic reconstruction (V. Ntziachristos et al., *Proc. Natl. Acad. Sci. U.S.A.* 101, 12294 (2004)). Even for microscopic imaging where existing fluorescent proteins are highly effective, mIFPs should reduce the contribution of cellular autofluorescence, enable excitation by cheap laser diodes, add new wavelengths for multicolor labeling, and accept resonance energy transfer from other dyes, fluorescent proteins, or bioluminescent proteins.

The usefulness of mIFPs in protein localization and trafficking may enable new medical, surgical, or diagnostic uses for in vivo imaging. For example, mIFPs that are localized in cancer cells could be used to guide excision of tumor bodies and margins during surgery, as the resulting fluorescence would indicate the boundaries of the tumor's infiltration into healthy tissue.

Biliverdin ("By") is uniquely advantageous as a cofactor because it is spontaneously and irreversibly incorporated into bacteriophytochromes, nontoxic at appropriate doses (R. Ollinger et al., *Antioxid. Redox. Signal* 9, 2175 (2007); N. Atsunori et al., *Gastroenterology* 127, 595 (2004)), nonfluorescent by itself, endogenously produced, and can be further supplemented either by expression of heme oxygenase or by direct administration of commercially available material. Heme oxygenase is an important enzyme in its own right and is involved in various diseases (N. G. Abraham, A. Kappas, *Pharmacol. Rev.* 60, 79 (2008)). Its cumulative activity could be monitored by mIFP fluorescence if apoprotein expression were in excess over BV.

More than 1500 bacteriophytochrome-like sequences are already available in the NCBI and CAMERA databases (D. B. Rusch et al., *PLoS Biol.* 5, e77 (2007)). These genes should provide raw material for selection and directed evolution of photochemical transducers based on a scaffold completely independent of the 11-stranded beta-barrel of coelenterate fluorescent proteins.

Preparation and Expression of Recombinant Nucleic Acids

To obtain high level expression of a cloned gene or genome, the nucleic acid can be cloned into an expression vector that contains a strong promoter to direct transcription, a transcription/translation terminator, and if for a nucleic acid encoding a protein, a ribosome binding site for translational initiation. Suitable bacterial promoters are well known in the art and described (e.g., in Sambrook et al., and Ausubel et al., supra. Bacterial expression systems for expressing the protein are available in, e.g., *E. coli, Bacillus sp.*, and *Salmonella* (Palva et al., *Gene* 22:229-235 (1983)); Mosbach et al., *Nature* 302:543-545 (1983)). Kits for such expression systems are commercially available. Eukaryotic expression systems for mammalian cells, yeast, and insect cells are well known in the art and are also commercially available. Retroviral expression systems can be used in the present invention.

Selection of the promoter used to direct expression of a heterologous nucleic acid depends on the particular application. In certain embodiments the promoter is preferably positioned about the same distance from the heterologous transcription start site as it is from the transcription start site in its natural setting. As is known in the art, however, some variation in this distance can be accommodated without loss of promoter function. Accordingly, in certain embodiments the promoter is positioned to yield optimal expression of the protein encoded by the heterologous nucleic acid. Heterologous refers to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

In addition to the promoter, in certain embodiments the expression vector also contains a transcription unit or expression cassette that contains all the additional elements required for the expression of the nucleic acid in host cells. A typical expression cassette thus contains a promoter operably linked to the nucleic acid sequence encoding the nucleic acid of choice and signals required for efficient polyadenylation of the transcript, ribosome binding sites, and translation termination. In certain embodiments, additional elements of the cassette can include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region can be obtained from the same gene as the promoter sequence or can be obtained from different genes.

One of skill in the art will know how to select an expression vector based on the size of the insert and the cell-type to be transfected or transformed. For example, any of the conventional vectors used for expression in eukaryotic or prokaryotic cells can be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags can be included in an expression cassette for nucleic acid rescue. Markers such as fluorescent proteins, green or red fluorescent protein, β-gal, CAT, and the like can be included in the vectors as markers for vector transduction.

In certain embodiments, regulatory elements can be incorporated into the expression vectors. Expression vectors containing regulatory elements include but are not limited to SV40 vectors, papilloma virus vectors, retroviral vectors, and vectors derived from Epstein-Barr virus. Other exemplary eukaryotic vectors include but are not limited to pMSG, pAV009/A+, pMT010/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

In certain embodiments expression of proteins from eukaryotic vectors can also be regulated using inducible promoters. With inducible promoters, expression levels are tied to the concentration of inducing agents, such as tetracycline, by the incorporation of response elements for these agents into the promoter. Generally, high level expression is obtained from inducible promoters only in the presence of the inducing agent; basal expression levels are minimal.

In certain embodiments, a multicistronic vector comprises a nucleic acid that encodes an IFP disclosed herein and one or more additional genes.

In certain embodiments the vector has a regulatable promoter, e.g., tet-regulated systems and the RU-486 system (see, e.g., Gossen & Bujard, *PNAS* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a sequence of choice under the direction of the polyhedrin promoter or other strong baculovirus promoters.

Additional elements that are incorporated into expression vectors include but are not limited to a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is based on various factors. For example, antibiotic resistance genes will be chosen and incorporated into an expression vector based on the organism and/or cell line that is to be transfected/transformed. In other examples, antibiotic resistance genes are chosen based on the a series of co-transfections and multi-gene selection criteria. The prokaryotic sequences are preferably chosen such that they do not interfere with the replication of the DNA in eukaryotic cells, if necessary.

Standard transfection and transformation techniques are known to one of skill in the art. These techniques can be used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). In certain embodiments, transformation and transfection of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (1983)).

Furthermore, one of skill in the art will know that any of the well-known procedures for introducing foreign nucleotide sequences into host cells (e.g., transformation or transfection) can be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing mIFP proteins and nucleic acids.

After the expression vector is introduced into the cells, the transfected cells are cultured under conditions favoring expression of the protein of choice, which is recovered from the culture using standard techniques identified below.

Both naturally occurring and recombinant mIFP proteins can be purified, for example, for use in diagnostic assays, for making antibodies (for diagnosis and therapy) and vaccines, and for assaying for anti-viral compounds. Naturally occurring protein can be purified from animal and plant tissue, e.g., from primate tissue samples. Recombinant protein can be purified from any suitable expression system.

Purification of IFPs

The mIFP protein can be purified to substantial purity by standard techniques, including selective precipitation (e.g., with such substances such as ammonium sulfate), column chromatography, immunopurification methods, and other techniques known to one of skill in the art (see, e.g., Scopes, *Protein Purification: Principles and Practice* (1982); U.S. Pat. No. 4,673,641; Ausubel et al., supra; and Sambrook et al., supra).

A number of procedures known to one of skill in the art can be employed when recombinant protein is being purified. For example, proteins having established molecular adhesion properties can be reversible fused to the protein. With the appropriate ligand or substrate, a specific protein can be selectively adsorbed to a purification column and then freed from the column in a relatively pure form. The fused protein is then removed by enzymatic activity. Finally, protein can be purified using immunoaffinity columns. Recombinant protein can be purified from any suitable source, include yeast, insect, bacterial, and mammalian cells.

Recombinant proteins can be expressed and purified by transformed bacteria in large amounts, typically after promoter induction; but expression can be constitutive. For example, promoter induction with IPTG is one example of an inducible promoter system. Bacteria are grown according to standard procedures in the art. Fresh or frozen bacteria cells are used for isolation of protein.

Proteins expressed in bacteria can form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCl pH 7.5, 50 mM NaCl, 5 mM MgCl2, 1 mM DTT, 0.1 mM ATP, and 1 mM PMSF. One of skill in the art will know that the stability of the protein will determine the lysis and purification buffer components. For example, one of skill in the art will know that protease inhibitor cocktails can be used to minimize and/or prevent protein degradation. Such protease inhibitor cocktails may include but are not limited to PMSF. Similarly, one of skill in the art will know that detergents and/or surfactants may be added to prevent protein aggregation, to enhance purification, and increase solubilization. Specifically, non-ionic, zwitterionic, and ionic detergents can be used. Such detergents and surfactants include but are not limited to Tween, Triton (e.g., Triton X-100), octylglucoside, DM, DDM, Chaps, Zwittergents (e.g., zwittergent 3-12), sodium deoxycholate, and glycerol. Furthermore, one of skill in the art will know that reducing agents can be used to prevent aggregation and enhance purification of proteins. Reducing agents include, but are not limited to, 2-mercaptoethanol, DTT, and TCEP. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies can be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation can occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify recombinant protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

Solubility fractionation can be used as a standard protein separation technique for purifying proteins. As an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

The protein can also be separated from other proteins on the basis of its size, net surface charge, hydrophobicity, and affinity for ligands or substrates using column chromatography. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

The invention provides kits for practicing the assays described herein. Kits for carrying out the diagnostic assays of the invention typically include a probe that comprises an antibody or nucleic acid sequence that specifically binds to polypeptides or polynucleotides of the invention, and a label for detecting the presence of the probe. The kits may include several antibodies or polynucleotide sequences encoding polypeptides of the invention, e.g., a cocktail of antibodies that recognize the proteins encoded by the biomarkers of the invention.

Diagnostic Tests & Imaging

In certain embodiments, a nucleic acid encoding any of the IFPs described herein, is used in an energy transfer experiment, wherein the energy transfer experiment is selected from the group consisting of fluorescence resonance energy transfer (FRET), luminescence resonance energy transfer (LRET), and bioluminescence resonance energy transfer (BRET). In certain embodiments, the IFPs used in an energy transfer experiment is supplied in a kit.

In certain embodiments, the nucleic acid to any of the IFPs described herein is used in a fluorescence resonance energy transfer (FRET) assay. In certain embodiments the assay comprises: a set of probes comprising at least a first and a second molecular probe, each molecular probe able to specifically bind a molecule of interest and each molecular probe associated with a fluorescent protein or dye, together, the dyes allow energy transfer, wherein at least one molecular probe comprises a reactive group to modulate the spatial organization of the molecular probes after binding to the molecule of interest; wherein the reactive group is not involved in binding to the molecule of interest; and wherein at least one of the fluorescent proteins is encoded by a nucleic acid that encodes one of the IPFs described herein.

In certain embodiments, the nucleic acid that encodes any of the IFPs described herein is used as a detection probe. In certain embodiments, any of the IFPs described herein is used as a detection probe for an in vitro diagnostic assay or test. In certain embodiments, any of the IFPs described herein is used as a detection probe for an in vivo diagnostic assay or test. In certain embodiments, the in vivo diagnostic assay or test is performed in a whole, living animal.

In certain embodiments, any of the IFPs described herein is used as a detection probe for an ex vivo diagnostic assay or test.

In certain embodiments, the IFP is conjugated to an antibody, a receptor, or a ligand. In certain embodiments, the antibody, receptor, or ligand detects a specific protein or cell type associated with a disease. In certain embodiments, the IFP detection probes are used to detect and diagnose a disease. In certain embodiments, the IFP detection probes are used to track the progression of a disease. In certain embodiments, the IFP detection probes are used to determine the prognosis of a disease based on disease state and progression. In certain embodiments, the IFP detection probes are used to track and determine the efficacy of a drug(s) and/or therapy(ies) in the treatment of a disease.

In certain embodiments the disease is a proliferative disease. In certain embodiments the disease is a muscle-related disease. In certain embodiments the disease is a gastro-intestinal related disease. In certain embodiments the disease is an inflammatory disease. In certain embodiments the disease is a neurological disease. In certain embodiments the disease is an ocular disease. In certain embodiments the disease is an autoimmune disease.

In certain embodiments, the IFP is conjugated to an antibody, a receptor, or a ligand that binds to and detects a cancer-related protein. In certain embodiments, the IFP is conjugated to an antibody, receptor, or ligand that binds to and detects a cancer cell biomarker that is expressed on the extracellular side of a cancer cell. In certain embodiments, the IFP detection probes are used to detect and diagnose cancer. In certain embodiments, the IFP detection probes are used to track the progression of a cancer. In certain embodiments, the IFP detection probes are used to determine the prognosis of a cancer based on disease state and progression. In certain embodiments, the IFP detection probes are used to track and determine the efficacy of a drug(s) and/or therapy(ies) in the treatment of a cancer. In certain embodiments the cancer is breast cancer, brain cancer, colon cancer, melanoma, leukemia (e.g., AML), pancreatic cancer, prostate cancer, ovarian cancer, lung cancer, and/or gastric cancer.

In certain embodiments, a pair of detection probes can be used for use in a diagnostic assay or test wherein one or more of the detection probes is one of the IFPs disclosed herein.

In certain embodiments, the IFPs described herein are used for fluorescent spectroscopy. In certain embodiments, the spectroscopy is in vitro spectroscopy. In certain embodiments, the spectroscopy is in vivo spectroscopy. In certain embodiments, the spectroscopy is ex vivo spectroscopy.

In certain embodiments the IFP-conjugates target and bind to tumor cells. In certain embodiments the IFP-conjugates are used for in vivo imaging during a surgical procedure to trace the boundaries of a tumor for tumor rescission. In certain embodiments the IFP-conjugates are used for in vivo imaging to trace the boundaries of a tumor in preparation for external radiation therapy.

In certain embodiments, the IFPs described herein are used for a time-resolved fluorescence immunoassay for multiple analytes. In certain embodiments, the time-resolved fluorescence immunoassay for multiple analytes, comprises the steps of: (a) forming an incubation mixture of: (i) antibodies against each analyte; (ii) a predetermined amount of fluorescently labeled analytes wherein each fluorescently labeled analyte has a different fluorescene lifetime; and (iii) a sample to be tested; (b) incubating the mixture under conditions and for a period of time sufficient for antibody and analytes to complex; and (c) determining contemporaneously the amount of each fluorescently labeled analyte bound with antibody as an indication of the amount of each corresponding analyte in the sample, by (i) exciting the fluorescently labeled analyte with a light pulse; and (ii) determining the amplitude of each fluorescence decay curve for the antibody-bound fluorescently labeled analyte by a single amplitude measurement measuring all of the fluorescence reaching the detector from the instant of excitation; wherein the fluorescently labeled analytes are labeled with a fluorophore encoded by a nucleic acid that encodes any of the IFPs described herein.

Companion Diagnostics

In other embodiments, this disclosure relates to companion diagnostic methods and products.

In one embodiment, the companion diagnostic method and products can be used to monitor the treatment of cancer. In a specific embodiment, the companion diagnostic method and products can be used to monitor the treatment of breast cancer. In a specific embodiment, the companion diagnostic method and products can be used to monitor the treatment of an autoimmune disease. In one embodiment, the companion diagnostic method and products can be used to monitor the treatment of brain cancer, colon cancer, melanoma, leukemia (e.g., AML), pancreatic cancer, prostate cancer, ovarian cancer, lung cancer, and/or gastric cancer. In one embodiment, the companion diagnostic method and products can be used to monitor the treatment of viral diseases. In one embodiment, the companion diagnostic method and products can be used to monitor the treatment of retroviral diseases.

In some embodiments, the companion diagnostic methods and products include molecular assays to measure levels of proteins, genes or specific genetic mutations. Such measurements can be used, for example, to predict whether a cancer drug or therapy will benefit a specific individual, to predict the effective dosage of a cancer drug or therapy, to monitor a cancer drug or therapy, adjust a cancer drug or therapy, tailor a cancer drug or therapy to an individual, and track cancer progression and remission.

As used herein, the terms "cancer drug" and "cancer therapy" refer to a single agent or a cocktail of agents administered to treat a cancer patient. The terms include, but are not limited to chemotherapy, radiotherapy, hormonal therapy, immunotherapy, and/or radiation.

Conventional chemotherapeutic agents include but are not limited to alkylating agents (e.g., cisplatin, cyclophosphamide, carboplatin, ifosfamide, chlorambucil, busulfan, thiotepa, nitrosoureas, etc.), anti-metabolites (e.g., 5-fluorouracil, azathioprine, methotrexate, fludarabine, etc.), plant alkaloids (e.g., vincristine, vinblastine, vinorelbine, vindesine, podophyllotoxin, paclitaxel, docetaxel, etc.), topoisomerase inhibitors (e.g., amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, plicamycin, etc.), and the like.

Conventional hormonal therapaeutic agents include, but not limited to, steroids (e.g., dexamethasone), finasteride, aromatase inhibitors, tamoxifen, and gonadotropin-releasing hormone agonists (GnRH) such as goserelin.

Conventional immunotherapeutic agents include, but not limited to, immunostimulants (e.g. Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., monoclonal antibodies which are conjugated to $^{111}$In, $^{90}$Y, or $^{131}$I).

Conventional radiotherapeutic agents include, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$mSn, $^{149}$Pm, $^{153}$Sm, $^{166}$Ho, $^{177}$Lu, $^{186}$Re, $^{188}$Re, $^{211}$At, and/or $^{212}$Bi, optionally conjugated to antibodies directed against tumor antigens.

Non-limiting examples of radiation therapy include but are not limited to x-ray therapy, gamma ray (gamma knife) therapy, and charged particle therapy. The radiation therapies may be administered via external-beam radiation or internally (i.e., internal radiation therapy or brachytherapy).

In certain embodiments, the IFPs described herein can be used to develop an individualized radiation plan for a patient. For example, a patient may be administered an IFP-antibody conjugate that bind cancer cells for detection using CT, MRI, PET, and Fluorescent Scan imaging.

In some embodiments, the compositions of the present invention comprise IFPs and IFP-conjugates and a physiologically (i.e., pharmaceutically) acceptable carrier. As used herein, the term "carrier" refers to a typically inert substance used as a diluent or vehicle for a drug such as a therapeutic agent. The term also encompasses a typically inert substance that imparts cohesive qualities to the composition. Typically, the physiologically acceptable carriers are present in liquid, solid, or semi-solid form. Examples of liquid carriers include physiological saline, phosphate buffer, normal buffered saline (135-150 mM NaCl), water, buffered water, 0.4% saline, 0.3% glycine, glycoproteins to provide enhanced stability (e.g., albumin, lipoprotein, globulin, etc.), and the like. Examples of solid or semi-solid carriers include mannitol, sorbitol, xylitol, maltodextrin, lactose, dextrose, sucrose, glucose, inositol, powdered sugar, molasses, starch, cellulose, microcrystalline cellulose, polyvinylpyrrolidone, acacia gum, guar gum, tragacanth gum, alginate, extract of Irish moss, panwar gum, ghatti gum, mucilage of isapol husks, Veegum®, larch arabogalactan, gelatin, methylcellulose, ethylcellulose, carboxymethylcellulose, hydroxypropylmethylcellulose, polyacrylic acid (e.g., Carbopol), calcium silicate, calcium phosphate, dicalcium phosphate, calcium sulfate, kaolin, sodium chloride, polyethylene glycol, and combinations thereof. Since physiologically acceptable carriers are determined in part by the particular composition being administered as well as by the particular method used to administer the composition, there are a wide variety of suitable formulations of pharmaceutical compositions of the present invention (see, e.g., Remington's Pharmaceutical Sciences, 17.sup.th ed., 1989).

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, eg., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged IFP-conjugate suspended in diluents, e.g., water, saline, or PEG 400; (b) capsules, sachets, or tablets, each containing a predetermined amount of a IFP-conjugate, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise an IFP-conjugate in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The IFP-conjugate may be made into aerosol formulations (i.e., "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged IFP-conjugate with a suppository base. Suitable suppository bases include natural or synthetic triglycerides or paraffin hydrocarbons. In addition, it is also possible to use gelatin rectal capsules which contain a combination of the IFP-conjugate of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a IFP-conjugate. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

EXAMPLES

The methods system herein described are further illustrated in the following examples, which are provided by way of illustration and are not intended to be limiting.

Example 1

Novel Truncation Mutant of a *Bradyrhizobium* sp. ORS278 Phytochrome mIFP is a novel truncation mutant of the phytochrome BrBphP from the bacterium *Bradyrhizobium* sp. ORS278 (Giraud et al., Nature 417:202-205 (2002)). mIFP is monomeric, and contains 320 amino acids starting from the first N-terminal amino acid from BrBphP. mIFP includes 19 mutations introduced through directed evolution. The 19 amino acid substitutions of mIFP are P2S, P8S, T14F, A74P, V107I, V128I, I146M, F156I, Y168V, H175N, V178I, P185A, D199T, R210H, L256M, N258D, D292H, A310T, E320K.

Figure 4:
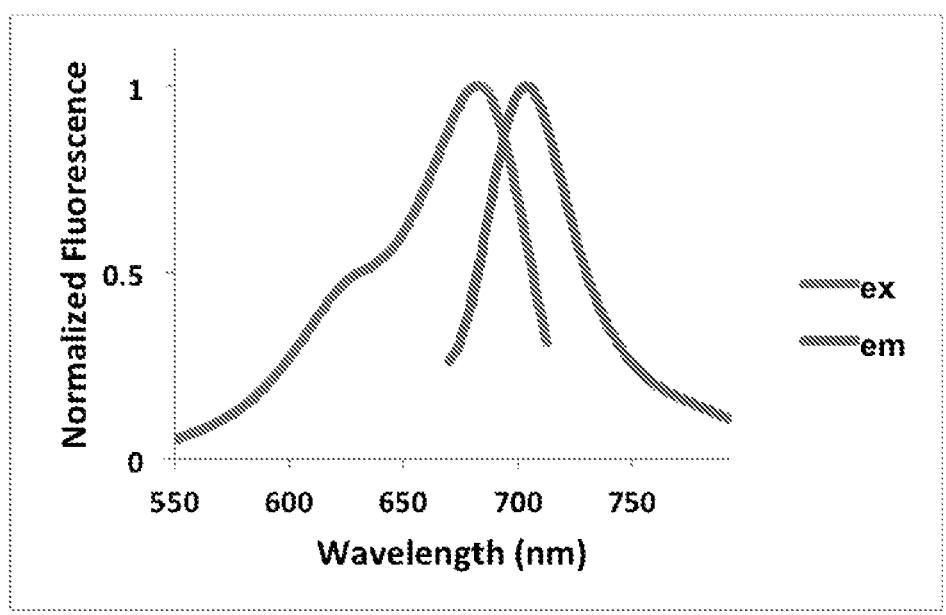
FIG. 4 illustrates the photophysical properties of mIFP. The normalized excitation spectra is the left-most spectra, and the emission spectra is the right-most spectra. The maximal excitation and emission wavelengths are 683 nm and 704 nm, respectively.
Figure 5:
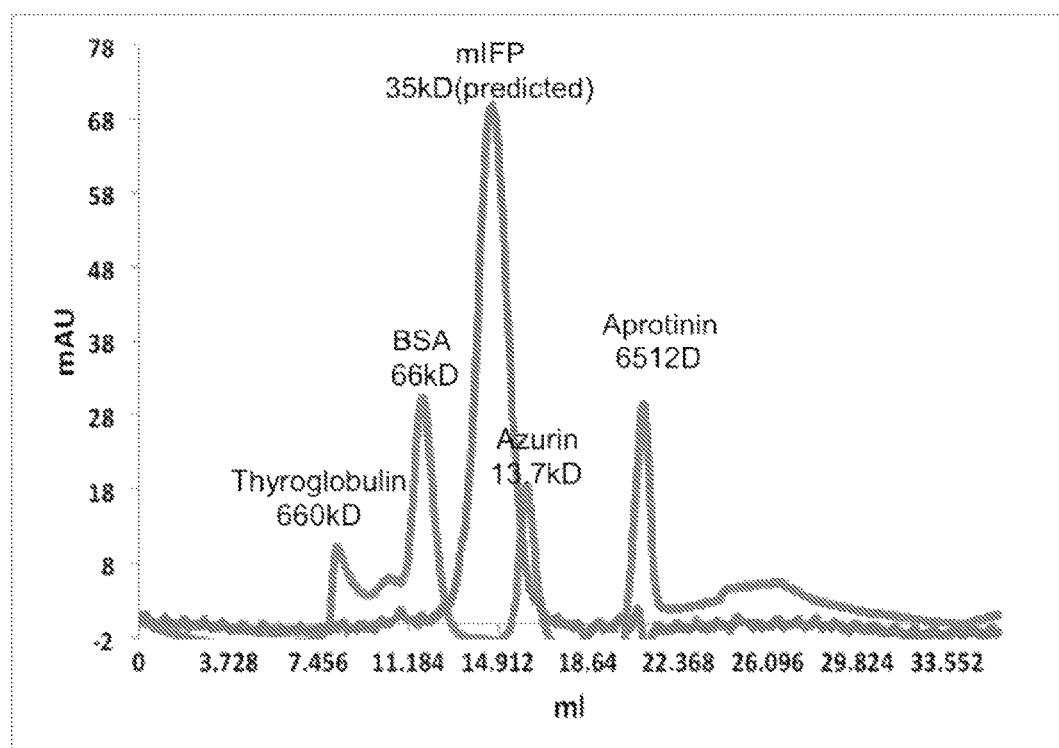
FIG. 5 illustrates the stoichiometry of mIFP. Gel filtration chromatography of mIFP shows that the molecular weight of mIFP is 35 kD as predicted based on its sequence. The protein molecular weight markers Thyroglobulin, BSA, Azurin, and Aprotinin are also shown.

When expressed in either bacteria or mammalian cells, these mutant phytochromes spontaneously incorporate biliverdin, a ubiquitous intermediate in heme catabolism, and become fluorescent. The maximal absorbance wavelength of mIFP is 683 nm (FIG. 3). The maximal excitation and emission wavelengths are 683 nm and 704 nm, respectively (FIG. 4). mIFP shows approximately a ten-fold increase in brightness compared to IFP1.4. Gel filtration chromatography of mIFP demonstrates that the molecular weight of mIFP is 35 kD (FIG. 5).

Example 2

Additional Truncation Mutants

Additional truncation mutants were developed from BrBphP. The mutations are relative to wild-type BrCBD, which is truncated from full length BrBphP.

BrIFPv1 includes a D199M substitution. The amino acid sequence of BrIFPv1 is provided as SEQ ID NO:3, and the nucleotide sequence of BrIFPv1 is provided as SEQ ID NO:4.

BrIFPv2 includes the following substitutions: A74P, V107I, V128I, I146M, P185A, M199T, R210H, L256M, N258D, D292H, E320K. The amino acid sequence of BrIFPv2 is provided as SEQ ID NO:5, and the nucleotide sequence of BrIFPv2 is provided as SEQ ID NO:6.

BrIFPv3 includes the following substitutions: A74P, V107I, V128I, I146M, P185A, M199T, R210H, L256M, N258D, D292H, E320K, T14F, F156I, H175N, and A310T. The amino acid sequence of BrIFPv3 is provided as SEQ ID NO:7, and the nucleotide sequence of BrIFPv3 is provided as SEQ ID NO:8.

Example 3

Figure 6:
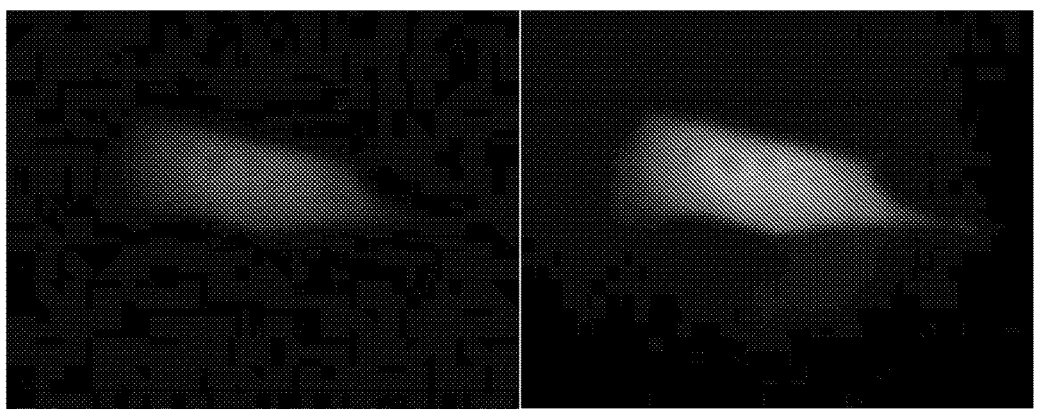
FIG. 6 illustrates mIFP as a genetically encoded tag for cellular and protein imaging. The left panel shows a HeLa cell expressing mIFP. The right panel shows the same HeLa cell expressing EGFP.

Mammalian Expression of mIFP Engineered from a Bacterial Phytochrome mIFP is a genetically encoded tag for cellular and protein imaging. FIG. 6 shows mIFP as a genetically encoded tag for cellular and protein imaging. mIFP was expressed in a HeLa cell (FIG. 6, left panel), which co-expresses with EGFP (FIG. 6, right panel).

Figure 7:
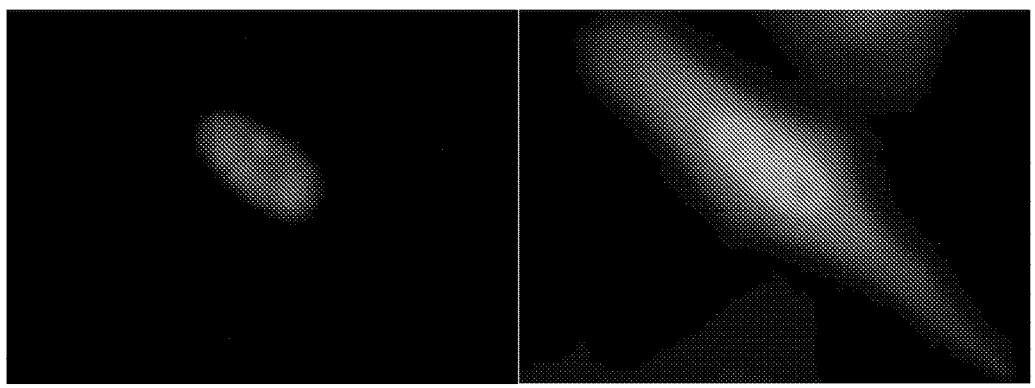
FIG. 7 illustrates mIFP as a genetically encoded tag for cellular and protein imaging. The left panel shows a Hela cell expressing an mIFP-H2B fusion. The right panel shows the same HeLa cell expressing EGFP (enhanced GFP). The mIFP-H2B fusion correctly localizes to the nucleus, whereas EGFP is localized to both the cytosol and nucleus.
Figure 8:
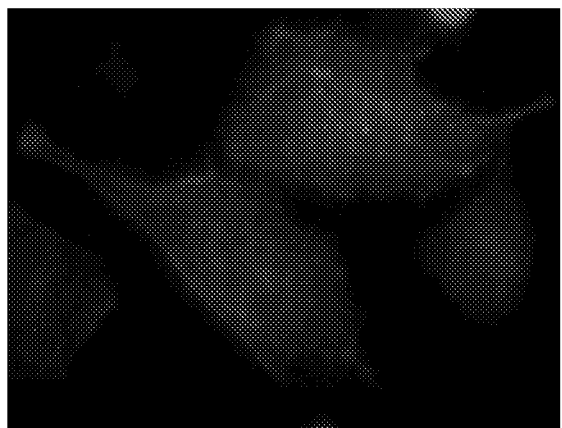
FIG. 8 illustrates HeLa cells expressing mIFP-LifeAct fusion proteins. MIFP-LifeAct correctly marks the F-acting filament in the cell.

Because mIFP is monomeric, mIFP can be used as a protein fusion tag with no or little perturbation of the protein of interest. mIFP was fused to H2B, and localized to the nucleus (FIG. 7, left panel). In contrast, the same cell shows EGFP localization to both the cytosol and nucleus (FIG. 7, right panel). mIFP was also fused to LifeAct, which localized to F-acting filaments in a HeLa cell (FIG. 8).

Example 4

Identification of a Naturally Monomeric BphP

Figure 9:
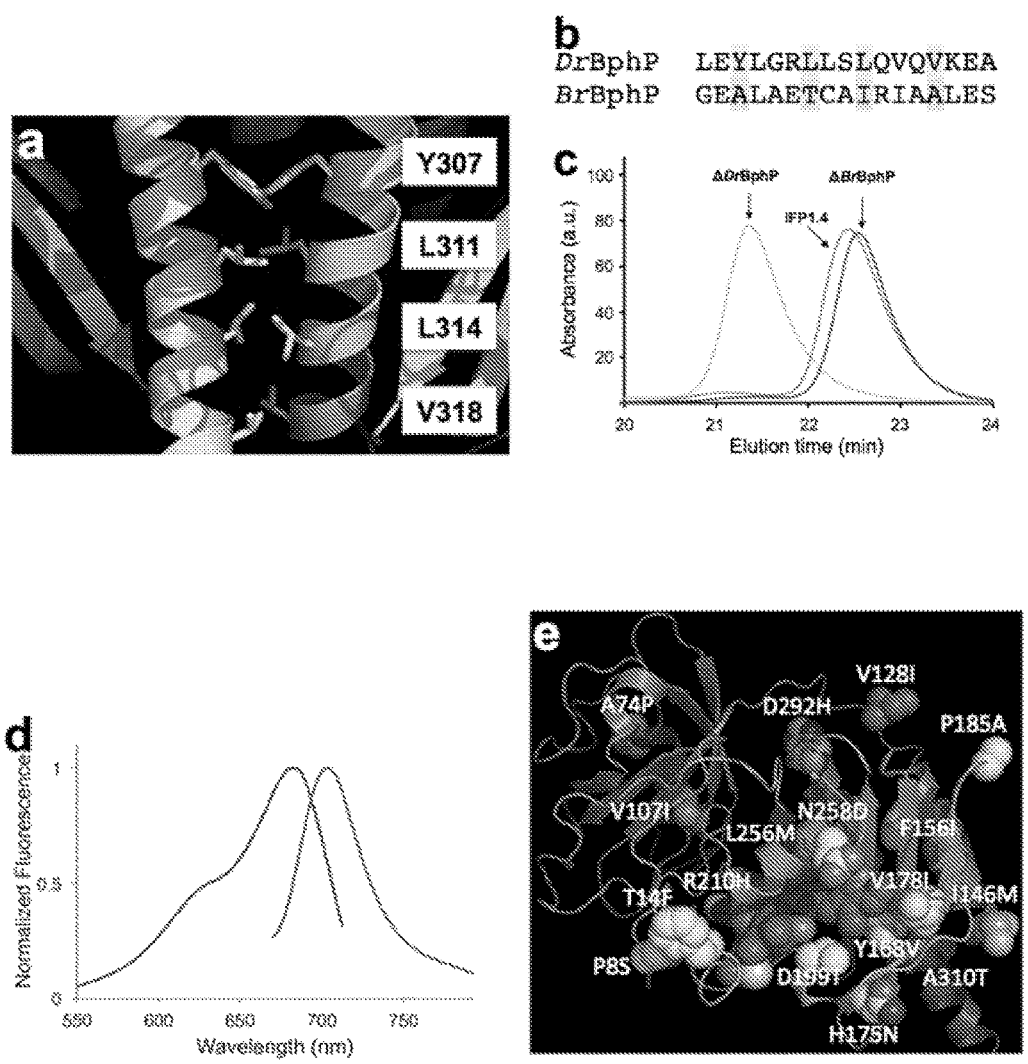
FIG. 9 shows the bioinformatic identification and protein engineering of a naturally monomeric bacterial phytochrome into a monomeric infrared fluorescent protein (mIFP). (a) Dimer interface of DrBphP (PDB: 2O9B). (b) Sequence alignment of DrBphP (a BphP from *Deinoccocus Radiodurans*) and BrBphP. Residues in the core of dimer interface of DrBphP are colored in yellow, and the corresponding residues in BrBphP in cyan. (c) Size exclusion chromatography of ΔBrBphP, ΔDrBphP and IFP1.4. (d) Excitation (blue) and emission (red) spectra of mIFP. (e) A structure model of mIFP with introduced mutations. The chromophore BV is shown in purple. (f) Fluorescence of purified mIFP against pH. (g) Comparison of cellular brightness among mIFP, iRFP and IFP1.4 in HeLa cells. (h) Representative fluorescence images of mIFP, iRFP and IFP1.4 in HeLa cells.
Figure 9:
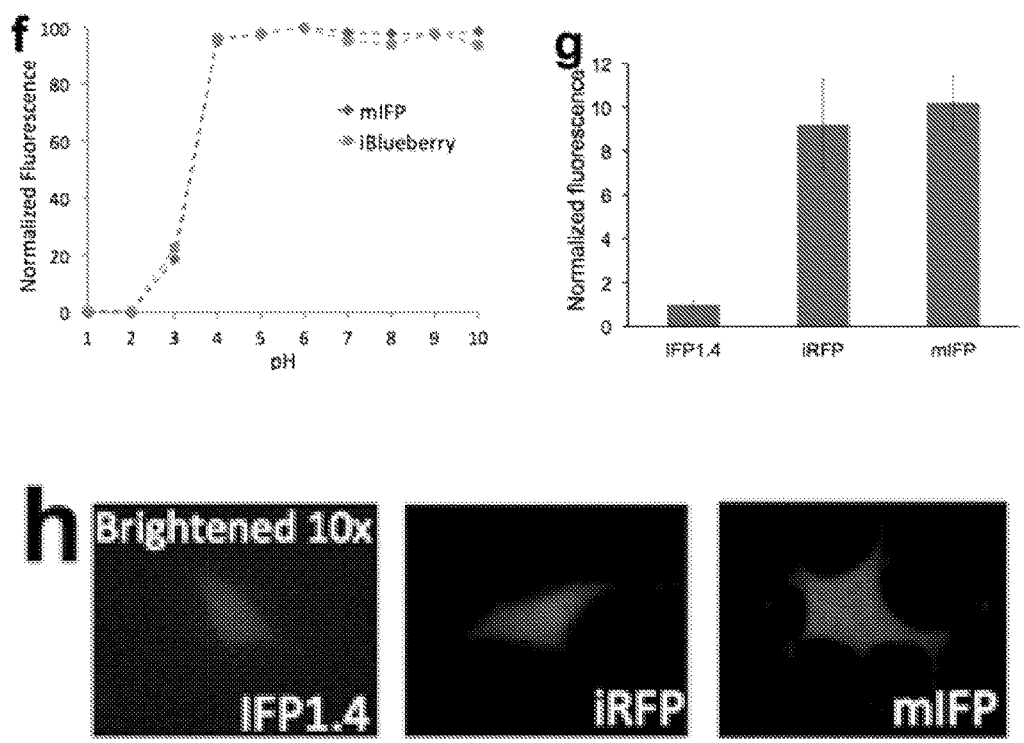

The crystal structure of several truncated BphPs (ΔBphP=PAS-GAF) is available, including ΔDrBphP, ΔRpBphP2, and ΔRpBphP3 (Wagner, J. R., Brunzelle, J. S., Forest, K. T. & Vierstra, R. D. A light-sensing knot revealed by the structure of the chromophore-binding domain of phytochrome. Nature 438, 325-331 (2005); Wagner, J. R., Zhang, J., Brunzelle, J. S., Vierstra, R. D. & Forest, K. T. High Resolution Structure of Deinococcus Bacteriophytochrome Yields New Insights into Phytochrome Architecture and Evolution. *J Biol Chem* 282, 12298-12309 (2006); Bellini, D. & Papiz, M. Z. research papers. *Acta Cryst* (2012). D68, 1058-1066 [doi:10.1107/S0907444912020537] 1-9 (2012). doi:10.1107/50907444912020537; Yang, X., Stojković, E. A., Kuk, J. & Moffat, K. Crystal structure of the chromophore binding domain of an unusual bacteriophytochrome, RpBphP3, reveals residues that modulate photoconversion. *Proc Natl Acad Sci USA* 104, 12571-12576 (2007)). All the three ΔBphPs form dimer through GAF domain via strong hydrophobic interaction. In ΔDrBphP, the core of the dimer interface is composed of four residues: Y307, L311, L314 and V318 (FIG. 9A).

L311 seems to play an essential role since a single mutation L311K turned a dimeric IFP1.2 into a monomer (Shu, X. et al. Mammalian expression of infrared fluorescent proteins engineered from a bacterial phytochrome. *Science* 324, 804-807 (2009)). The derived mutant IFP1.3, however, tended to aggregate when expressed at high concentration in mammalian cells. This is likely because simple disruption of the dimer interface exposes all hydrophobic residues that were previously buried, resulting in poor solubility of the protein. Indeed, further engineering of the rest three residues improved solubility and the derived mutant IFP1.4 could be expressed at high level (Shu, X. et al. Mammalian expression of infrared fluorescent proteins engineered from a bacterial phytochrome. *Science* 324, 804-807 (2009)). But IFP1.4 is problematic when fused to certain proteins. This is probably because a lot more than four residues are buried in the dimer interface. In principle, one can engineer the entire dimer interface to obtain a well-behaved mutant as a protein tag. Such engineering, however, would be tedious due to large number of residues involved. Furthermore, simple mutations of hydrophobic residues to hydrophilic ones may perturb protein folding and reduce protein stability. Therefore, this application describes an alternative strategy: identify and engineer a naturally monomeric ΔBphP into a monomeric IFP.

The protein sequence database such as NCBI (National Center for Biotechnology Information) or CAMERA (Community Cyberinfrastructure for Advanced Microbial Ecology Research & Analysis) contains hundreds to thousands of BphP sequences. The hypothesis of this experiment was that some of the sequences might be monomeric, at least for the ΔBphP. If this is true, a potentially monomeric ΔBphP is then expected to have no strong hydrophobic interaction at the area corresponding to the dimer interface of ΔDrBphP. By analyzing ~40 BphP sequences from NCBI, BrBphP (a BphP from *Bradyrhizobium*) was identified as a potential candidate (Giraud, E. et al. Bacteriophytochrome controls photosystem synthesis in anoxygenic bacteria. *Nature* 417, 202-205 (2002)).

In BrBphP, the corresponding residue of the hydrophobic leucine 311 in DrBphP is a polar residue threonine (FIG.

9B), which suggests that ΔBrBphP may be monomeric since our results demonstrated that L311K mutation is sufficient to disrupt the dimer interface of ΔDrBphP. Furthermore, alanine is found in both positions corresponding to tyrosine 307 and valine 318. Alanine is less hydrophobic than valine, and has higher average surface accessibility (or surface exposure) than tyrosine and valine based on previous structural analysis of thousands of proteins (Moelbert, S. Correlation between sequence hydrophobicity and surface-exposure pattern of database proteins. *Protein Science* 13, 752-762 (2004); Lee, B. & Richards, F. M. The interpretation of protein structures: estimation of static accessibility. *J Mol Biol* 55, 379-400 (1971)). Although the corresponding position of L314 is isoleucine, it is not rare to find hydrophobic residues on the surface of a soluble protein, which contribute to protein stability via partial burial of hydrophobic surface (Jacak, R., Leaver-Fay, A. & Kuhlman, B. Computational protein design with explicit consideration of surface hydrophobic patches. *Proteins* 80, 825-838 (2011)).

Accordingly, synthesized DNA of ΔBrBphP proteins was prepared and purified. Size exclusion chromatography (SEC) showed that ΔBrBphP was eluted at later time than the dimeric ΔDrBphP, and at similar time of the monomeric IFP1.4 (FIG. 9C). This result suggests that ΔBrBphP is monomeric.

Example 5

Directed Evolution of mIFP

The non-fluorescent ΔBrBphP was engineered into a fluorescent mIFP via directed evolution using structure-guided engineering and DNA shuffling of improved mutants (Stemmer, W. P. Rapid evolution of a protein in vitro by DNA shuffling. *Nature* 370, 389-391 (1994)). mIFP has excitation and emission maxima of 683 and 704 nm (FIG. 9D); quantum yield 8%; extinction coefficient 88,000 $M^{-1}cm^{-1}$. mIFP has 320 residues. The holo-protein's molecular weight (Mw) is 35.69 kDa. Nineteen mutations were introduced into mIFP (FIGS. 1 and 2) and their locations were determined based on a modeled structure (FIG. 9E) (Schwede, T. SWISS-MODEL: an automated protein homology-modeling server. *Nucleic Acids Res* 31, 3381-3385 (2003)): four of them are located in the PAS domain (P2S is not shown); the rest are in the GAF domain (E320K is not shown). Mutations of five residues were found near the D-ring: N258D sits on the top of the D-ring; Y168V and V178I at the bottom; D199T at the side of the D-ring. These residues are highly conserved in BphPs (>97%) based on analysis of 41 BphP sequences, and therefore are likely evolved for the biological function that involves cis→trans conformational change of BV through D-ring rotation (Yang, X., Ren, Z., Kuk, J. & Moffat, K. Temperature-scan cryocrystallography reveals reaction intermediates in bacteriophytochrome. *Nature* 479, 428-432 (2011)). Mutations of these residues likely rigidify the D-ring, and thus increase radiative decay of the excited state and contribute to the engineered fluorescence. mIFP is also monomeric based on SEC with measured Mw 35.16 kDa, which is close to the calculated Mw. mIFP fluorescence is stable over wide range of pH from 4 to 10 (FIG. 9F). Molecular brightness of mIFP is close to that of IFP1.4 and iRFP. Its cellular brightness is comparable to iRFP and significantly brighter (~10 fold) than IFP1.4 (FIGS. 9G and 9H).

Example 6 mIFP Overcomes the Problem of IFP1.4 and iRFP as a Protein Tag mIFP as a robust fusion tag. To verify that mIFP is a protein tag as robust as GFP, mIFP was fused to various proteins, which localized properly in mammalian cells: i) cytoskeleton proteins including actin, tubulin, keratin and nuclear lamin, which correctly labels actin filaments, microtubules and intermediate filaments in cytosol and nucleus; ii) cytoskeleton binding proteins including MAP Tau (microtubule-associated protein Tau), Lifeact and EB3, which binds to microtubule, F-actin and plus end of microtubule; iii) focal adhesions including paxillin, zyxin and VASP; iv) contractile proteins including myosin and α-actinin; v) DNA-binding proteins including histone and centromere protein B, which correctly labels chromosome at multiple cell-cycle stages and centromere; vi) nuclear pore complex such as NUP50 (nucleoporin 50 kDa) with correct localization at nuclear envelope; vii) cell junctions such as connexin 43, which forms gap junctions between HeLa cells.

It was also demonstrated that mIFP could be used to mark various subcellular organelles or compartments: i) mitochondria including outer membrane and matrix using TOMM20 (translocase of outer mitochondrial membrane 20) and PDHA (pyruvate dehydrogenase A); ii) ER using calnexin or CytERM (cytoplasmic end of an ER signal-anchor transmembrane protein); iii) Golgi using Golgi-targeting sequence or MannII (alpha-mannosidase II), a Golgi resident key enzyme involved in N-linked glycosylation; iv) endosome; v) lysosome using LAMP (lysosome associated membrane glycoprotein); vi) peroxisome using PMP (peroxisomal membrane protein); vii) clathrin-coated vesicles using light-chain clathrin; viii) plasma membrane using farnesylation signal from c-Ha-Ras, or c-Src (Src family of tyrosine kinases) via its N-terminal myristoylation signal.

Example 7 mIFP Expressed in Model Organisms

GFP has been successfully used in model organisms since its fluorescence only requires molecular oxygen for chromophore maturation, which significantly expands its utility in cell biology (Tsien, R. Y. The green fluorescent protein. *Annu Rev Biochem* 67, 509-544 (1998)). In contrast to GFP, mIFP fluorescence requires biliverdin, a derivative of heme. Since multicellular organisms contain heme oxygenase (Cui, L. et al. Biochemical and Biophysical Research Communications. *Biochem Biophys Res Commun* 377, 1156-1161 (2008); Poss, K. D. & Tonegawa, S. Heme oxygenase 1 is required for mammalian iron reutilization. *Proc Natl Acad Sci USA* 94, 10919-10924 (1997)) and require hemeproteins to conduct essential biological functions such as oxygen transport by hemoglobin and cellular respiration by cytochrome in the respiratory electron transfer chain of mitochondria, we reasoned that mIFP might be fluorescent in these organisms. The feasibility of using mIFP in *Drosophila*, zebrafish and mouse using histone-mIFP fusions is demonstrated herein.

Figure 10:
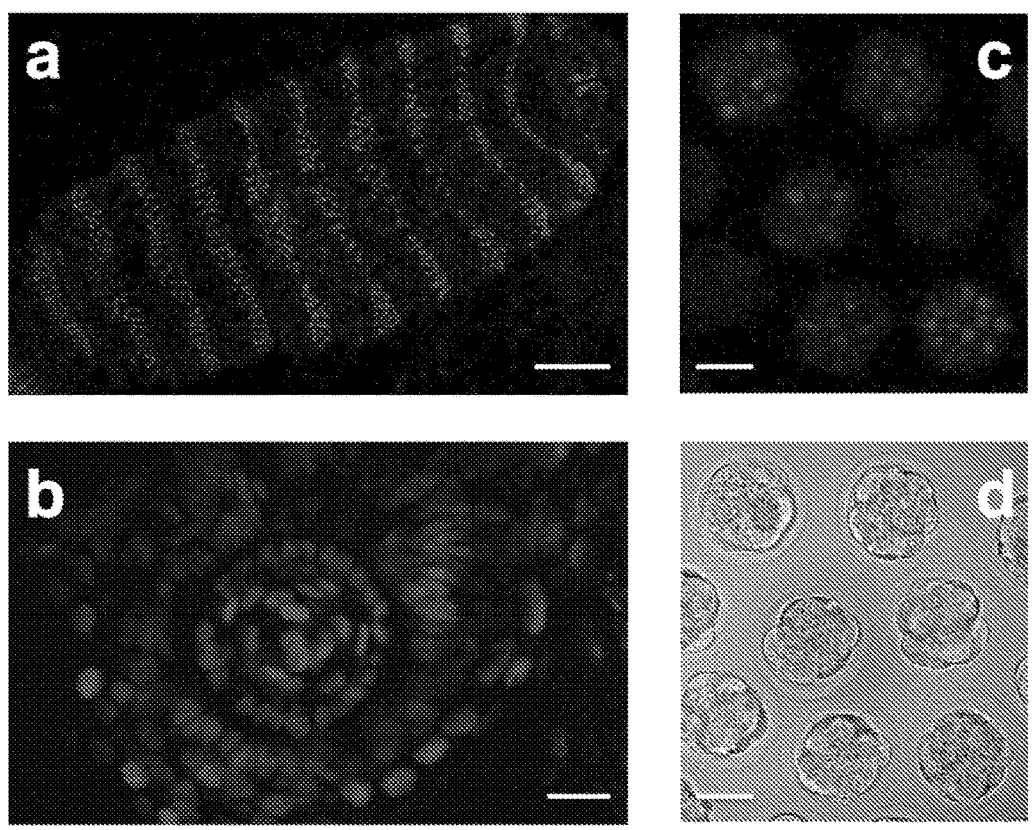
FIG. 10 shows the expression of mIFP-histone fusion in model organisms. (a) UAS-mIFP-histone 3.3 driven by engrailed-Gal4 in *Drosophila* larvae. (b) Fluorescence image of zebrafish eye area expressing mIFP-H2B. (c) Fluorescence and (d) brightfield images of mIFP-H2B in mouse embryo. Scale bar, 50 μm (a, c, d); 15 μm (b).

For *Drosophila*, a UAS-mIFP-histone 3.3 transgenic line was created. This line was crossed with engrailed-Gal4 line to drive the expression of mIFP fusion with well-known pattern. Confocal imaging of the embryo indicated bright nuclear mIFP fluorescence with expected segmental pattern throughout the epithelial tissue (FIG. 10A). For zebrafish, mIFP-H2B was expressed by mRNA injection. Imaging near the eye area at 30 hpf revealed bright nuclear mIFP fluorescence with a structure resembling an eye and surrounding tissue (FIG. 10B). mIFP-H2B was also in mouse embryo with nuclear fluorescence.

Example 8

Rational Design of a Blueshifted mIFP (iBlueberry)

mIFP provides an orthogonal color to GFP as a protein fusion tag based on successful demonstration in cultured cells and the model organisms. While the GFP family covers the spectrum every 30 nm from 400 to 600 nm, mIFP absorbs at 683 nm. To bridge this gap and add another orthogonal color in protein labeling, a blueshifted mutant of mIFP was designed.

Figure 11:
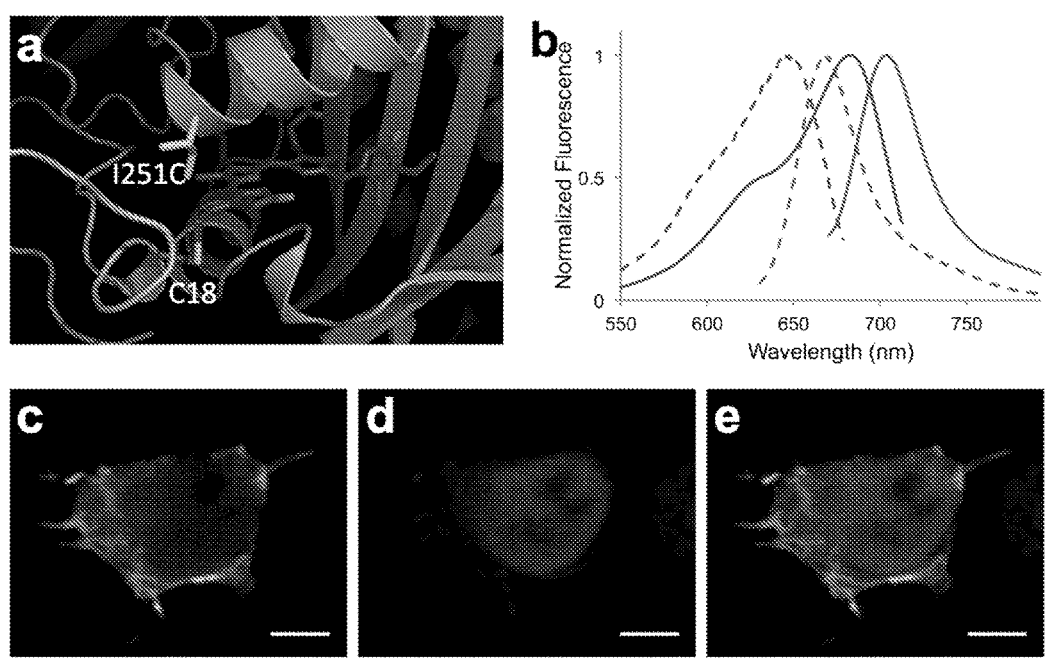
FIG. 11 shows the rational design of a blueshifted mIFP (iBlueberry) for two-color protein labeling with mIFP. (a) A modeled structure of mIFP showing residue I251 that is mutated to cysteine in iBlueberry. The chromophore BV is shown in purple, together with the conserved cysteine 18. (b) Excitation (blue) and emission (red) spectra of iBlueberry (dashed line), compared to those of mIFP (solid line). (c-e) Fluorescence images in the iBlueberry channel (c), mIFP channel (d), and overlay (e) of Lifeact-iBlueberry and mIFP-H2B co-expressed in HEK293 cells. Fluorescence in the iBlueberry and mIFP channels is shown by green and red pseudo-color, respectively. iBlueberry channel: excitation by 640 nm laser, emission 661±10 nm; mIFP channel: excitation by 640 nm, emission 732±34 nm). Scale bar, 5 μm.
Figure 12:
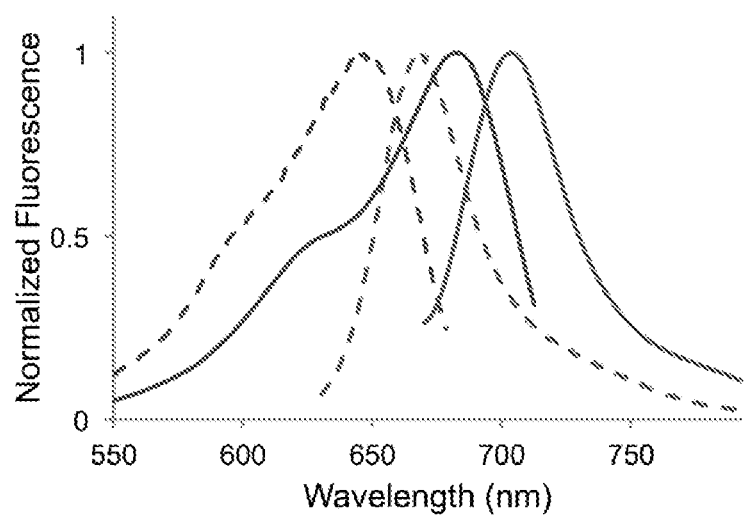
FIG. 12 shows the normalized excitation (first dashed line on the left) and emission (second dashed line from the left) spectra. The maximal excitation and emission wavelengths are 644 nm and 663 nm respectively. As a comparison, excitation and emission spectra of mIFP are also shown in first and second solid lines, respectively.
Figure 13:
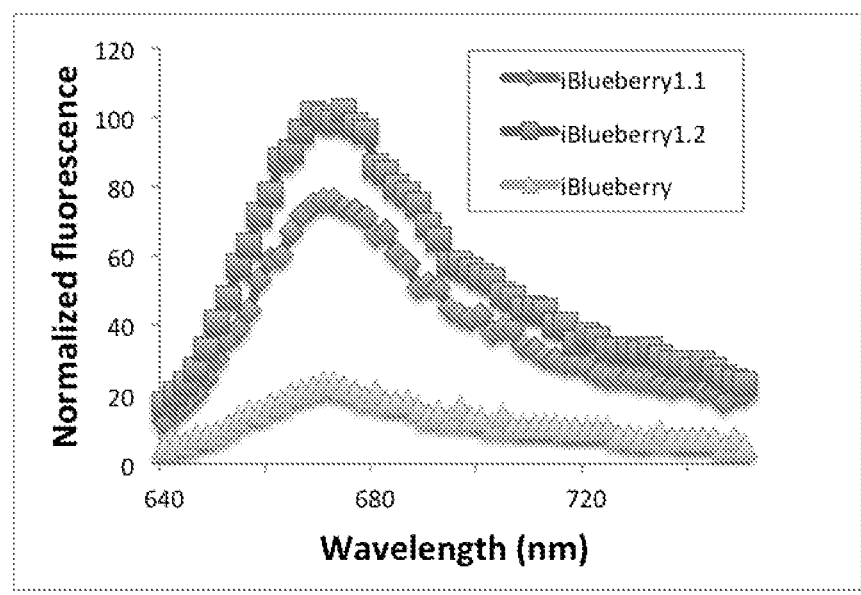
FIG. 13 shows brighter mutants of iBlueberry. iBlueberry1.1 (SEQ ID NOs: 11 and 12) and iBlueberry1.2 (SEQ ID NOs: 13 and 14 are significantly brighter than iBlueberry (SEQ ID NOs: 9 and 10).
Figure 14:
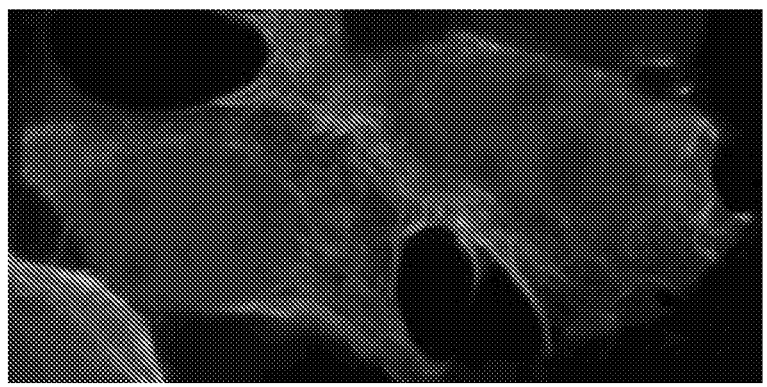
FIG. 14 shows that iBlueberry can be genetically encoded as a tag for cellular and protein imaging. LifeAct is fused to iBlueberry and is expressed in HEK293 cells. iBlueberry-LifeAct correctly labels actin filament in the cell.

It is known that a fluorophore's spectra depend on its conformation. For example, large bathochromic shift of rhodopsin was explained by twist of a double bond in the chromophore, which disturbs π-conjugation and reduces conjugation efficiency (Kakitani, T. & Kakitani, H. THEORETICAL STUDY OF OPTICAL SPECTRA AND CONFORMATION OF THE CHROMOPHORE OF HYPSORHODOPSIN. *Photochem Photobiol* 32, 707-709 (1980)). To induce blue shift, the mIFP chromophore BV, which is composed of four rings, was examined. The A, B and C rings are in the same plane, whereas the D-ring is tilted. They are conjugated to each other via a double bond between them. The A-ring is covalently linked to the protein by a thioether bond with the conserved cysteine 18 (C18) at N-terminus. Based on structural analysis of residues surrounding the A-ring, it was determined that isoleucine 251 (I251) is located on opposite side of the A-ring plane relative to C18 (FIG. 11A).

Accordingly, it was hypothesized that by mutating I251 to cysteine, it would be possible to tilt the A-ring and twist the double bond between A and B rings, if this cysteine could react with the A-ring. This rational design strategy is simple but risky since molecular mechanism of the thioether linkage formation in BphPs is not clear. Surprisingly, mIFP is significantly blue shifted (~40 nm) by a single mutation I251C (FIG. 11B), suggesting that BV prefers to attach to the new cysteine rather than the conserved cysteine. This blueshifted mutant of mIFP is termed iBlueberry. iBlueberry has excitation and emission maxima of 644 and 668 nm; quantum yield 8%; extinction coefficient 80,000 M-1cm-1. Its fluorescence is also stable over wide range of pH from 4 to 10, similar to mIFP.

To confirm that C251 does form a covalent bond with BV, C18 was mutated to Ile. The excitation and emission spectra of the double mutant (I251C/C18I) are similar to those of the single mutant, suggesting that BV is not linked to C18 in the single mutant. The covalent attachment of BV by zinc-induced fluorescence assay was then examined, which is based on the phenomena that bilin-zinc ion complex is orange fluorescent upon UV illumination (Berkelman, T. R. & Lagarias, J. C. Visualization of bilin-linked peptides and proteins in polyacrylamide gels. *Analytical Biochemistry* 156, 194-201 (1986)). It was observed that for mIFP and the two mutants, zinc-induced orange fluorescence was at the same position as the protein band with Coomassie blue staining, demonstrating that BV is covalently attached to the protein since the holoproteins were denatured in the assay. On the other hand, mIFP C18A mutant did not show such co-localization. Because residue 251 is relatively further away from the A-ring compared to C18, the iBlueberry A-ring is tilted which reduces its conjugation with the other rings and results in the blueshift. The exact details would require structural studies and theoretical calculations that one of skill in the art could readily perform. It is noteworthy to point out that, in Cphs, the residue at position 251 is cysteine that forms a thioether bond with the A-ring of phycocyanobilin, another tetrapyrrole bilin (Ulijasz, A. T. & Vierstra, R. D. Phytochrome structure and photochemistry: recent advances toward a complete molecular picture. *Curr Opin Plant Biol* 14, 498-506 (2011); Rockwell, N. C. The Structure of Phytochrome: A Picture Is Worth a Thousand Spectra. *THE PLANT CELL ONLINE* 18, 4-14 (2006)).

Additional iBlueberry mutants include but are not limited to iBlueberry 0.1 (iBlueberry with one mutation C18I); iBlueberry0.2 (iBlueberry with one mutation C18L); iBlueberry0.3 (iBlueberry with one mutation E177G); iBlueberry1.1 (iBlueberry with 3 mutations: E158V, A185S, and I203N); iBlueberry1.2 (iBlueberry with 4 mutations: F10Y, G63D, D150N, and F190L); iBlueberry2.1 (iBlueberry with 6 mutations: F10Y, G63D, D150N, A185S, I203N, and V213L); iBlueberry2.2 (iBlueberry with 4 mutations: E158V, A185S, I203N, and K320* (stop codon), i.e. truncation of K320); iBlueberry2.3 (iBlueberry with 10 mutations: F10Y, A13E, G63D, D150N, A185S, I203N, C251Y, V261I, E312G, and Q316* (stop codon), i.e. truncation of 316 to 320); iBlueberry2.4 (iBlueberry with 3 mutations: E158V, F190L, and Q227E); iBlueberry2.5 (iBlueberry with 3 mutations: T6I, E158V, and F190L); and iBlueberry2.6 (iBlueberry with 5 mutations: F10Y, G63D, E158V, A185S, and I203N). All mutants described herein can be made as IFP-conjugates for each and every method and use described herein.

Example 9

Two-Color Protein Labeling by iBlueberry and mIFP

Since the spectra of iBlueberry and mIFP are well separated, their application in two-color protein labeling was demonstrated. iBlueberry was fused to Lifeact that labels F-actin, and mIFP to H2B that labels nucleus. Confocal imaging of HEK293 cells expressing both constructs revealed that F-actin and nucleus were well distinguished in two imaging channels optimized for iBlueberry and mIFP respectively (FIG. 11C-11E). This result demonstrates that iBlueberry and mIFP provides two orthogonal colors to GFP and its red homologs in protein labeling.

The engineered mIFP and iBlueberry provide two orthogonal colors in labeling proteins. They also open opportunities of developing other FP-based technologies such as FRET reporters and Brainbow (Livet, J. et al. Transgenic strategies for combinatorial expression of fluorescent proteins in the nervous system. *Nature* 450, 56-62 (2007)).

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

We claim:

1. A variant polypeptide of a parent polypeptide,
   wherein said variant polypeptide comprises at least 90% identity to SEQ ID NO:2,
   wherein the variant polypeptide comprises at least one amino acid substitution at a position selected from the group consisting of position 2, 8, 14, 74, 107, 128, 146, 156, 168, 175, 178, 185, 199, 210, 256, 258, 292, 310, and 320, wherein the numbering of the amino acid positions correspond to that in native BrBphP from *Bradyrhizobium* sp. ORS278, and
   wherein the variant polypeptide is an infrared fluorescent polypeptide.

2. The variant polypeptide of claim 1, wherein said variant polypeptide comprises at least 95% identity to SEQ ID NO:2.

3. The variant polypeptide of claim 1, wherein said variant polypeptide comprises SEQ ID NO:2.

4. The variant polypeptide of claim 1, wherein the variant polypeptide comprises at least one amino acid substitution selected from the group consisting of 2S, 8S, 14F, 74P, 107I, 128I, 146M, 156I, 168V, 175N, 178I, 185A, 199T, 210H, 256M, 258D, 292H, 310T, and 320K.

5. The variant polypeptide of claim 4, wherein the variant polypeptide comprises the amino acid substitutions 2S, 8S, 14F, 74P, 107I, 128I, 146M, 156I, 168V, 175N, 178I, 185A, 199T, 210H, 256M, 258D, 292H, 310T, and 320K.

6. The variant polypeptide of claim 1, wherein the variant polypeptide further comprises amino acid substitution I251C.

7. The variant polypeptide of claim 1, wherein the polypeptide comprises an amino acid sequence selected from the group consisting of SEQ ID NOS: 10, 12, 14, 16, 18, 20, 22, 24, and 26.

* * * * *